United States Patent
Weirich et al.

(10) Patent No.: US 11,137,541 B2
(45) Date of Patent: Oct. 5, 2021

(54) DELIVERY FIBER ASSEMBLY AND A BROAD BAND SOURCE

(71) Applicant: NKT PHOTONICS A/S, Birkerød (DK)

(72) Inventors: Johannes Weirich, Copenhagen N (DK); Martin Dybendal Maack, Kgs Lyngby (DK)

(73) Assignee: NKT PHOTONICS A/S, Birkerod (DK)

( * ) Notice: Subject to any disclaimer, the term of this patent is extended or adjusted under 35 U.S.C. 154(b) by 0 days.

(21) Appl. No.: 16/871,297

(22) Filed: May 11, 2020

(65) Prior Publication Data

US 2020/0341190 A1   Oct. 29, 2020

Related U.S. Application Data

(63) Continuation of application No. 15/738,623, filed as application No. PCT/DK2016/050221 on Jun. 24, 2016, now Pat. No. 10,649,136.

(30) Foreign Application Priority Data

Jun. 25, 2015 (DK) .......................... PA 2015 70393

(51) Int. Cl.
*G02B 6/02* (2006.01)
*G02B 6/024* (2006.01)
(Continued)

(52) U.S. Cl.
CPC ........ *G02B 6/02357* (2013.01); *A61B 5/0066* (2013.01); *G01B 9/02091* (2013.01);
(Continued)

(58) Field of Classification Search
CPC .......................... G02B 6/02357; G02B 6/2938; G02B 6/2821; G02B 6/29389; G02B 6/024; G02B 6/02347
See application file for complete search history.

(56) References Cited

U.S. PATENT DOCUMENTS

| 6,901,197 B2 | 5/2005 | Hasegawa et al. |
| 7,289,709 B2 | 10/2007 | Folkenberg et al. |

(Continued)

FOREIGN PATENT DOCUMENTS

| EP | 2081074 A1 | 7/2009 |
| EP | 2533081 A1 | 12/2012 |

(Continued)

OTHER PUBLICATIONS

Extended European Search Report dated Jan. 17, 2019, issued by the European Patent Office in corresponding European Application No. 16813773.5-1230 (6 pages).

(Continued)

*Primary Examiner* — Sung H Pak
*Assistant Examiner* — Hoang Q Tran
(74) *Attorney, Agent, or Firm* — Buchanan Ingersoll & Rooney P.C.

(57) ABSTRACT

The invention comprises a delivery fiber assembly suitable for delivering broad band light. The delivery fiber assembly comprises a delivery fiber and a connector member. The deliver has a length, an input end for launching light and a delivery end for delivering light, where the delivery fiber comprises along its length a core region and a cladding region surrounding the core region. The cladding region comprises a cladding background material having a refractive index $N_{bg}$ and a plurality of inclusions of solid material having refractive index up to $N_{inc}$ and extending in the length of the longitudinal axis of the delivery fiber, wherein (Continued)

$N_{inc} < N_{bg}$ and the plurality of inclusions in the cladding region is arranged in a cross-sectional pattern comprising at least two rings of inclusions surrounding the core region. The connector is mounted to the delivery fiber at a delivery end section of the delivery fiber comprising said delivery end. The delivery fiber has a transmission bandwidth of about 200 nm or more, such as of about 300 nm or more, such as of about 400 nm or more, such as of about 500 nm or more.

6 Claims, 14 Drawing Sheets

(51) Int. Cl.
*A61B 5/00* (2006.01)
*G01B 9/02* (2006.01)
*G02B 6/28* (2006.01)
*G02B 6/293* (2006.01)
*G02B 21/00* (2006.01)
*G02B 23/24* (2006.01)
*H01S 3/23* (2006.01)

(52) U.S. Cl.
CPC ......... *G02B 6/024* (2013.01); *G02B 6/02347* (2013.01); *G02B 6/02361* (2013.01); *G02B 6/2821* (2013.01); *G02B 6/2938* (2013.01); *G02B 6/29389* (2013.01); *G02B 21/0032* (2013.01); *G02B 23/2469* (2013.01); *H01S 3/2308* (2013.01)

(56) References Cited

U.S. PATENT DOCUMENTS

| | | | |
|---|---|---|---|
| 8,731,009 | B2 | 5/2014 | Buchter |
| 8,849,083 | B1 | 9/2014 | Samson et al. |
| 9,048,627 | B2 | 6/2015 | Andersen et al. |
| 2005/0213103 | A1 | 9/2005 | Everett et al. |
| 2007/0013921 | A1 | 1/2007 | Pellemans et al. |
| 2007/0242923 | A1 | 10/2007 | Fini |
| 2008/0124036 | A1 | 5/2008 | Miyabe et al. |
| 2009/0168149 | A1* | 7/2009 | Petersson ........... G02B 6/02323 359/339 |
| 2011/0020008 | A1 | 1/2011 | Dong et al. |
| 2011/0188825 | A1* | 8/2011 | Alkeskjold ........ G02B 6/02333 385/126 |
| 2012/0188632 | A1 | 7/2012 | Dong et al. |
| 2012/0195554 | A1 | 8/2012 | Maack |
| 2018/0188447 | A1 | 7/2018 | Weirich et al. |

FOREIGN PATENT DOCUMENTS

| | | |
|---|---|---|
| JP | 2002537575 A | 11/2002 |
| JP | 2004220026 A | 8/2004 |
| JP | 2007108642 A | 4/2007 |
| JP | 2011107687 A | 6/2011 |
| JP | 2011257589 A | 12/2011 |
| JP | 2014132287 A | 7/2014 |
| WO | 0049436 A1 | 8/2000 |
| WO | 2004019092 A1 | 3/2004 |
| WO | 2011023201 A1 | 3/2011 |
| WO | 2012168400 A1 | 12/2012 |
| WO | 2015003714 A1 | 1/2015 |
| WO | 2015003715 A1 | 1/2015 |
| WO | 2015077021 A1 | 5/2015 |
| WO | 2015084198 A1 | 6/2015 |

OTHER PUBLICATIONS

Buczynski, R. et al., "Dispersion management in soft glass all-solid photonic crystal fibres", Opto-Electronics Review, vol. 20, No. 3, 2012, pp. 207-215.
Chen, M-Y., "All-solid silica-based photonic crystal fibers", Science Direct, Optics Communications, vol. 266, 2006, pp. 151-158.
Office Action (First Office Action) dated Jul. 30, 2019, by the China National Intellectual Property Administration in corresponding Chinese Patent Application No. 201680037135.2 and an English Translation of the Office Action. (22 pages).
Search Report dated Jan. 25, 2016, by the Danish Patent and Trademark office in corresponding Patent Danish Application No. PA 2015 70393. (4 pages).
Notification of Transmittal of the International Search Report (Form PCT/ISA/220 and PCT/ISA/210) and Written Opinion (Form PCT/ISA/237) dated Sep. 21, 2016, by the International Search Authority in corresponding International Application No. PCT/DK2016/050221. (14 Pages).
Pniewski, J. et al., "Nonlinear phenomena in all solid photonic crystal fibers with nanostructured core", Proc. of SPIE, vol. 8697, 2012, pp. 86971G-1-86971G-8.
Wong, L. et al., "Phosphate ytterbium-doped single-mode all-solid photonic crystal fiber with output power of 13.8 W", Scientifci Repor, vol. 5, No. 8490, 2015, pp. 1-4.
Xian, F. et al., "Solid microstructured optical fiber", vol. 11, No. 18, Sep. 8, 2003, Optics Express, pp. 2225-2230.
Yablon, A. D., et al., "Low-Loss High-Strength Microstructured Fiber Fusion Splices Using GRIN Fiber Lenses", 2004 Optical Society of America, 3 pages.
Office Action (Second Office Action) dated Mar. 24, 2020, by the China National Intellectual Property Administration in corresponding Chinese Patent Application No. 201680037135.2 and an English Translation of the Office Action. (13 pages).
Valerii (Vartan) Ter-Mikirtychev "Fundamentals of Fiber Lasers and Fiber Amplifiers" Springer International Publishing Company, Switzerland, 2014, 4 pages.
Office Action (Fourth Office Action) dated Jul. 29, 2020 by the China National Intellectual Property Administration of the People's Republic of China in corresponding Chinese Patent Application No. 201680037135.2, and an English Translation of the Office Action. (13 pages).
Office Action (Notice of Reasons for Refusal) dated Jun. 2, 2020, by the Japanese Patent Office in corresponding Japanese Patent Application No. 2017-566732, and an English Translation of the Office Action. (8 pages).

* cited by examiner

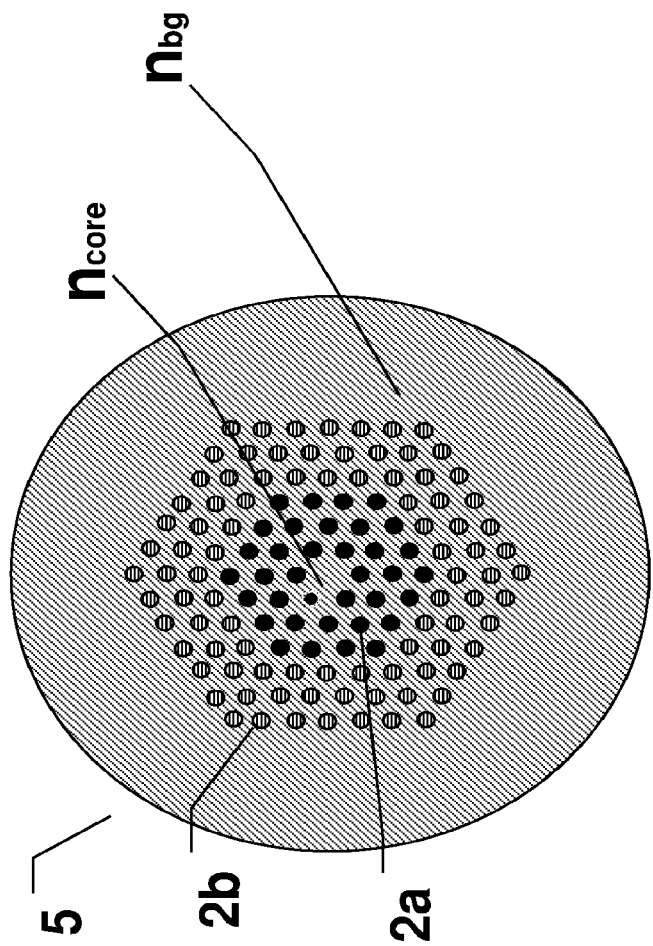

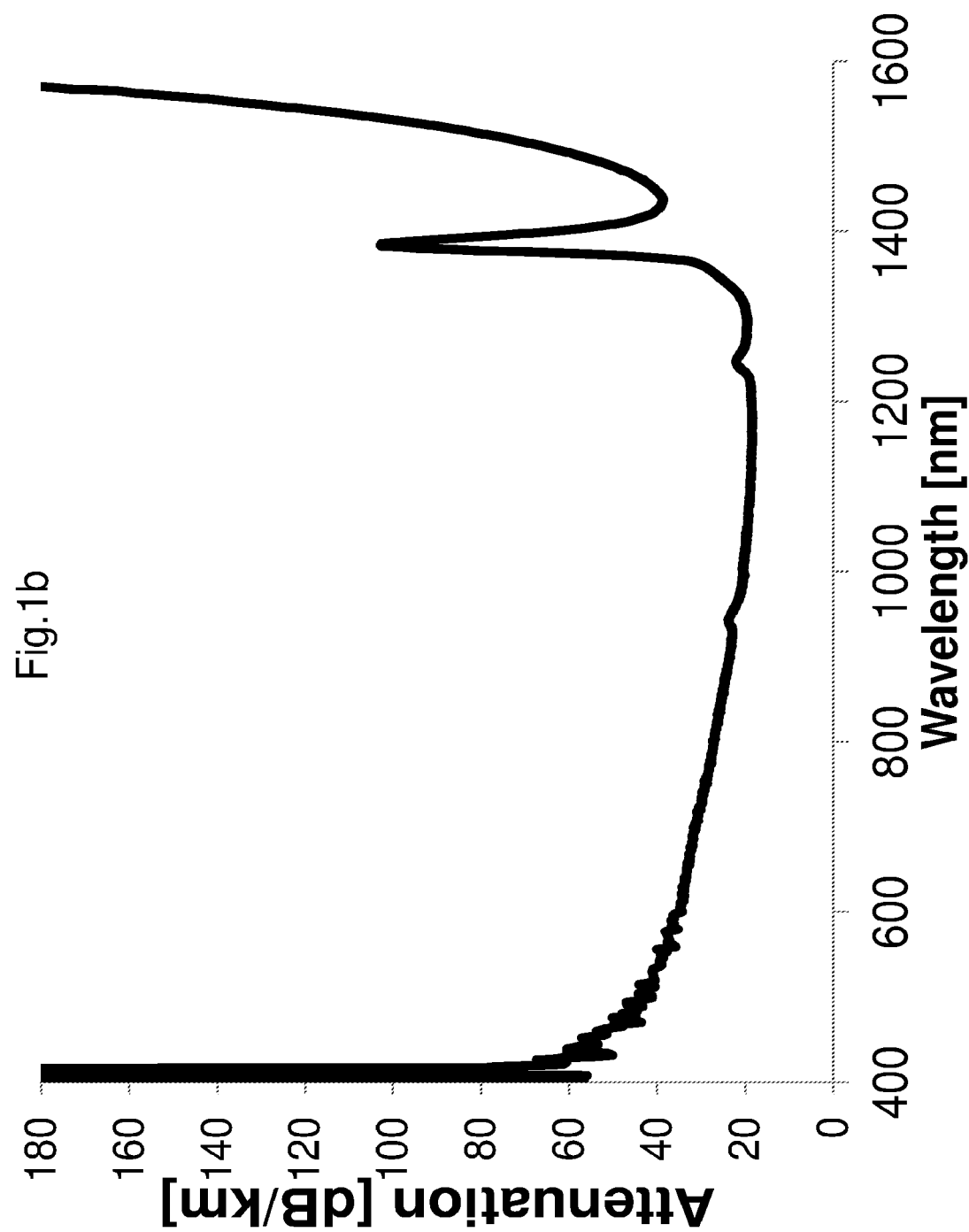

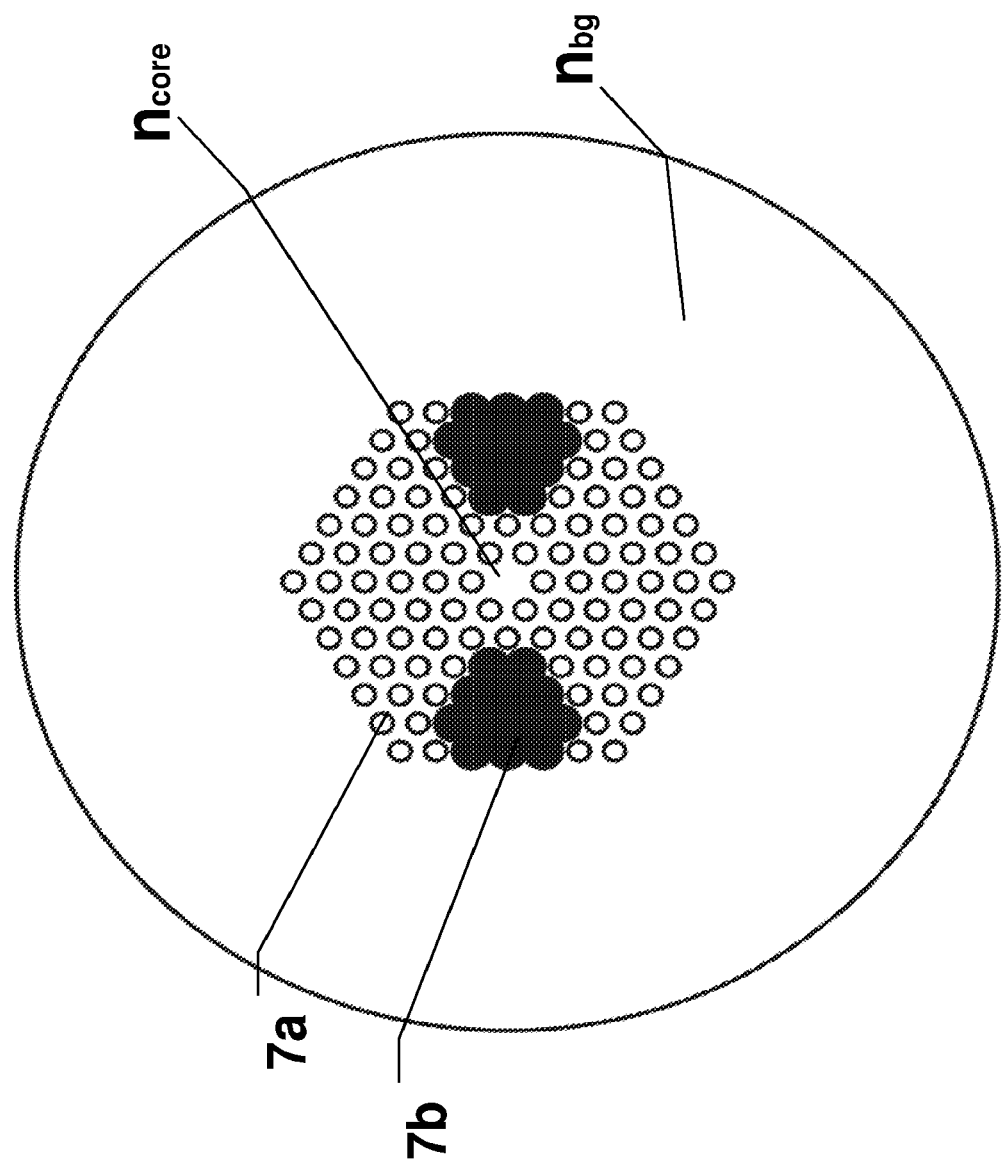

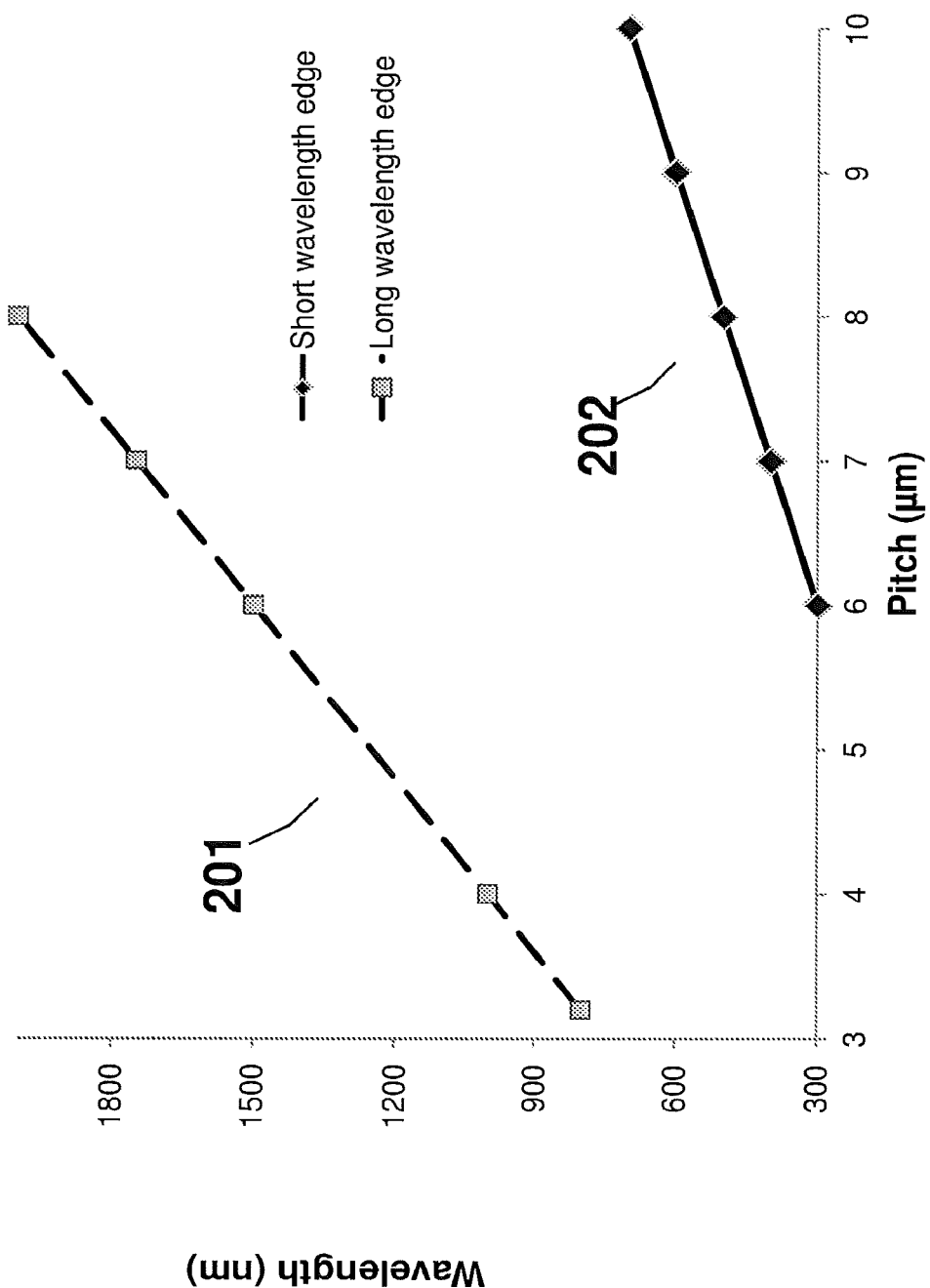

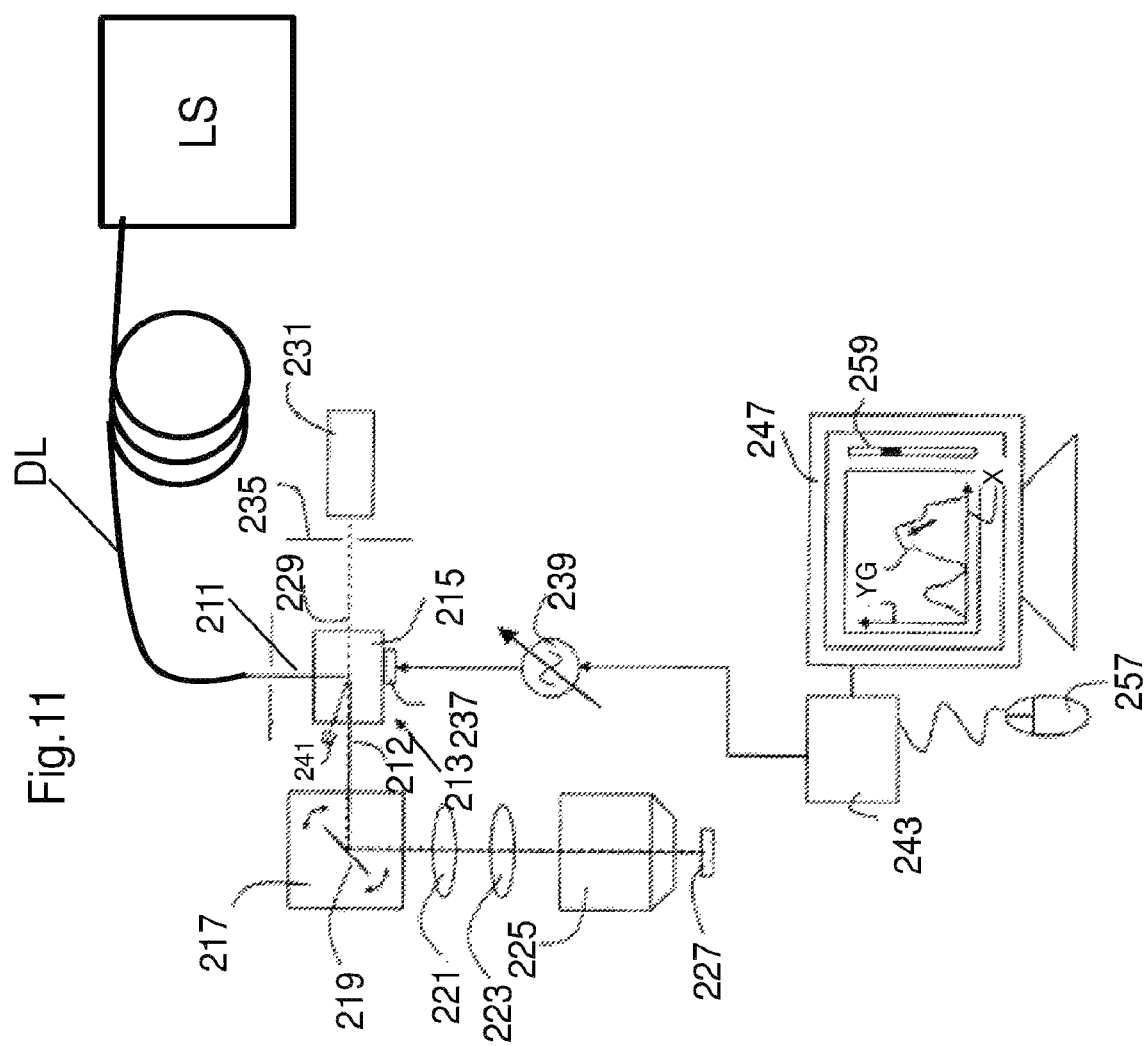

DELIVERY FIBER ASSEMBLY AND A BROAD BAND SOURCE

CROSS-REFERENCE TO RELATED APPLICATIONS

The present application is a continuation of U.S. Ser. No. 15/738,623, filed on 21 Dec. 2017, which is a national stage application of PCT/DK2016/050221, filed on 24 Jun. 2016, which claims the benefit of the Danish Patent Application No. PA 2015 70393, filed on 25 Jun. 2015. The foregoing applications are hereby incorporated by reference.

TECHNICAL FIELD

The invention relates to a delivery fiber suitable for delivering light from as broad band source as well as a broad band source system, and an apparatus comprising such broad band source.

BACKGROUND ART

Broad band sources and systems are well known in the art and are for example described in EP2081 074, WO15003714 and WO15003715.

WO15003714 discloses a supercontinuum light source comprising a microstructured optical fiber and a pump light source, where the microstructured optical fiber comprises an intermediate tapered section. Thereby a very broad and stable supercontinuum of light is obtained.

U.S. Pat. No. 8,731,009 discloses a super continuum light source comprising a pump source and a generator fiber for generating the supercontinuum, where the refractive index profile of the core of the generator fiber is arranged to allow modal cleaning of the light as it propagates to provide an optical super continuum with relatively high spectral density and/or good beam quality.

In general most of the prior art broad band sources are focused on generating supercontinuum light of high quality and/or which is spanning over increasingly broader band width, e.g. supercontinuum which is spanning further into the blue wavelength e.g. below 450 nm or even lower.

The generated light or fractions thereof are often used in high precision illumination procedures and/or high precision measuring procedures such as for stimulated emission depletion, for fluorescence imaging procedures for Optical Coherence Tomography (OCT) and/or for industrial inspection, such as metrology.

Usually the light or fractions of light generated by the broad band source is transmitted via a delivery fiber to an apparatus, such as an illumination apparatus and/or a measuring apparatus for use in the measuring process of the apparatus. Generally it is desired that the delivery fiber is simple to connect to the apparatus and it is well known in the art to use standard connectors such as connectors according to the standards IEC 61754-20, IEC 61754-15 or IEC 61754-13.

The prior art delivery fibers have usually been step index fibers having a relatively very narrow transmission band with because such fibers are easy to handle, easy to connectorize and have low transmission loss. In order to be capable of transmitting a broader band width is has been suggested to use of photonic crystal fiber (PCF) with air holes in their cross-sections as delivery fiber has been introduced; thereby the delivery fiber is capable of transmitting a broader band width. However, such holey PCF generally is difficult to connect and may result in undesired power loss.

DESCRIPTION OF THE INVENTION

An object of the present invention is to provide a delivery fiber assembly suitable for delivering broad band light from a broad band source and/or from two or more sources as well as a broad band source system where the delivery fiber is simple to connect to an apparatus for transmitting light to the apparatus and where at least one of the problems discussed above is alleviated.

It is further an object to provide a broad band source and a broad band source system comprising a delivery fiber which is simple to connect e.g. to an apparatus for transmitting light to the apparatus and where at least one of the problems discussed above is alleviated.

In an embodiment it is an object to deliver light by the delivery fiber from two or more light sources having different wavelength(s).

These and other objects have been solved by the invention or embodiments thereof as defined in the claims and as described herein below.

It has been found that the invention or embodiments thereof have a number of additional advantages which will be clear to the skilled person from the following description.

According to the invention it has been found that by providing a new type of delivery fiber for delivering broad band light or selected portions of broad band light comprising wavelengths e.g. discrete wavelengths within a broad range. The delivery fiber can be connectorized in a relatively simple and effective way and with a very low loss. Simultaneously it has been found that the novel delivery fiber assembly has a relatively high mechanical strength, which in fact is highly beneficial because such delivery fibers usually are subjected to mechanical disturbances such as bends and rough handling. Often the delivery is coiled and uncoiled repeatedly and with no control of coiling diameter.

In an embodiment of the delivery fiber assembly of the invention it is adapted for delivering broad band light to an apparatus for transmitting light to the apparatus. The delivery fiber assembly comprises a delivery fiber and a connector member. The delivery fiber has a length, an input end for launching light and a delivery end for delivering light. The delivery fiber comprises along its length a core region and a cladding region surrounding the core region wherein the cladding region comprises a cladding background material having a refractive index $N_{bg}$ and a plurality of microstructures in the form of inclusions of solid material having refractive index of up to $N_{inc}$ and extending in the length of and preferably along the longitudinal axis of the delivery fiber, wherein $N_{inc} < N_{bg}$. The plurality of inclusions in the cladding region is arranged in a cross-sectional pattern (a pattern seen in a cross section of the delivery fiber) comprising at least two rings of inclusions surrounding the core region. The connector member is mounted to the delivery fiber at a delivery end section of the delivery fiber comprising the delivery end. Further, the delivery fiber has a transmission bandwidth of about 200 nm or more, such as of about 300 nm or more, such as of about 400 nm or more, such as of about 500 nm or more for example at least an octave (halving/doubling in frequency).

Generally it is desired that the core region has a diameter up to about 15 μm

In an embodiment the transmission bandwidth is defined as the wavelengths where the delivery fiber has a transmission loss of less than 0.5 dB/m. In an embodiment the transmission bandwidth is defined as the wavelengths where the delivery fiber has a transmission loss of than less than 0.1 dB/m. Advantageously the transmission loss is measured when the fiber is bend with either a 16 cm or a 32 cm bending diameter.

Heretofore it has never been considered to use an all solid fiber comprising solid inclusions as delivery fiber for delivering light from a broad band source to an apparatus for measurement and/or illumination. In particular it has never been considered that such all solid fiber comprising solid inclusions could be constructed to have a transmission bandwidth of 200 nm or larger and in particular it is surprising that the all solid fiber comprising solid inclusions can be constructed to have a transmission bandwidth of 200 nm or less, below 1800 nm or even below 900 nm.

The term "inclusions" means inclusions in a background material, wherein an inclusion has another refractive index than that of the background material surrounding it. The solid inclusions can for example be inclusions of another glass type than the background material and/or an inclusion of doped material (index changing materials such as F, Ge, P, B) a vacuum inclusion or any combinations thereof. The inclusions of a delivery fiber can be of equal or different material or structure. An inclusion may be of a homogeneous material or it may have regions of different materials and/or refractive index. Where an inclusion comprises several regions of different refractive index the refractive index of the inclusion is determined as the average refractive index of the inclusion.

In the context of the present application, the phrase "ring of inclusions" refers to the cladding inclusions typically having substantially equal radial distance to the core and being aligned in a ring configuration surrounding the core. Typically, a ring of inclusions is not fully circular, but rather is shaped with a number of soft angles, such as in a hexagonal shape. Preferably all the inclusions of a ring of inclusions are of substantially the same size and preferably of same material.

The phrase "radial distance" means distance determined in radial direction from the longitudinal axis of the core of the delivery fiber.

The term "substantially" should herein be taken to mean that ordinary product variances and tolerances are comprised.

The diameter of the core and of an inclusion is determined as the characteristic diameter of the core/inclusion. The core or the inclusions are not always entirely circular. The characteristic diameter is the diameter of the circle of the inclusion/core where it is circular or in case the inclusion is not circular, the characteristic diameter is determined as the average of the maximum and the minimum extent of the inclusion/core in question.

The inclusions may have equal or different diameters and the inclusion diameter of the respective inclusions may as mentioned be equal or differ along the length of the fiber.

In an embodiment the delivery end section of the delivery fiber comprising the delivery end, and the connector member is mounted at a mounting distance from the delivery end such that the delivery end is passing through the connector member for connecting the delivery end in physical contact with a receiver waveguide, preferably a receiver fiber, such as a receiver fiber incorporated in an apparatus for illumination and/or metrology and/or surgery.

The delivery end of the fiber is the end facet. The mounting distance to the delivery end is usually a few mm e.g. at least 2 mm, such as up to 2 cm or preferably less than 1 cm. The mounting distance to the delivery end is usually given by the structure of the connector member. Preferably the connector member is a standard connector member such as a standard connector member according to at least one of the standards IEC 61754-20, IEC 61754-15 or IEC 61754-13 or equivalent standards. The mounting distance from the delivery end is determined as the distance from the delivery end to the nearest physical contact to the connector member. Usually the connector member has a connecting flange that extends beyond the delivery end for being mated with and connected to another connector member while simultaneously protecting the connected delivery end. Prior to being connected to the apparatus the delivery end is desirably protected by a removable cap. For optimal connection the delivery end is advantageously polished and optionally arranged to have a facet which is angled e.g. up to 60 degrees, such as up to about 30 degrees, such as from about 3 to 10 degrees, such as about 8 degrees relative to the cross-section plan of the fiber so as to reduce undesired reflection of light at the end facet. For broad band operation the angle of the facet is often selected as a compromise. Thus it is generally desired to have the facet angle sufficiently large enough to ensure that an undesired amount of light not to be reflected and thereby that a large amount of the light is collected within the NA of the fiber.

On the other hand the facet angle should advantageously not be too large because that may result in an undesired angular dispersion.

In an embodiment the delivery end section of the delivery fiber is mounted to the connector member such that the delivery end of the delivery fiber is suitable for connectorisation, without changing the fiber waveguide structure.

According to the present invention it has been found that the delivery fiber of the delivery fiber assembly can be connected to an apparatus without the use of free space optics—i.e. without the transmission at the connection site is outside the fiber—and without undesired change of the phase front of the propagating mode. Further the delivery fiber of the delivery fiber assembly can be connected to an apparatus without undesired expansion of mode field and thereby loss of light can be reduced or entirely avoided.

In an embodiment the connector member is mounted to the delivery fiber at the delivery end section of the delivery fiber at a distance to the delivery end, such that the delivery end is passing through the connector member for connecting the delivery end in physical contact with a receiver waveguide, preferably a receiver fiber, such as a receiver fiber incorporated in an apparatus for illumination and/or metrology and/or surgery.

The connector member preferably comprises a ferrule and the delivery end section passes through the ferrule for being coupled to the receiver unit.

Advantageously the connector member is arranged such that the delivery end can be brought in physical contact with and connected to a receiving waveguide e.g. an optical fiber comprising a corresponding receiving waveguide connector member.

Advantageously the connector member is spring-loaded, so the delivery end facet can be mated to a receiving fiber in a butt coupling where fiber faces are pressed together when the connectors are mated. The resulting glass-to-glass contact eliminates signal losses that would be caused by an air gap between the joined fibers.

In an embodiment the delivery fiber has, at least along its delivery end section and optionally along the entire length of the fiber, a constant mode field diameter for at least one wavelength within the transmission bandwidth where the mode field is expanding the fiber may lose light. The delivery end section preferably comprises a length of the fiber of at least 2 mm, preferably at least about 5 mm, such as at least 1 cm. Preferably the delivery fiber has a constant mode field diameter to wavelength profile within the transmission bandwidth at least along the delivery end section. The phrase 'mode field diameter to wavelength profile' means the profile of the respective mode field diameters relative to the respective wavelengths within the transmission bandwidth. Thereby the delivery fiber can be connected to an apparatus for use with a minimum loss of light.

The mode field diameters of the delivery fiber are advantageously selected in dependence on the desired transmission wavelength bandwidth. It has been found that the mode field diameter for a wavelength range of wavelengths below 2 µm varies surprisingly little. Thus for a bandwidth of 100 nm the mode field diameter varies preferably less than 10% based on the mode field diameter of the lowest wavelength.

It has been found that the relatively small core region i.e. about 15 µm or smaller is an important factor for keeping the mode field diameter range for the transmission bandwidth narrow. Thus, by selecting even smaller core region the mode field diameter range for the transmission bandwidth may be even narrower. Further it has been found that the mode field diameter variation is smaller for wavelength of about 900 nm or less than for larger wavelengths.

The delivery fiber may be tailored by selecting a mode field diameter range i.e. In an embodiment the delivery fiber at least along said delivery end section has a mode field diameter range for said transmission wavelength, wherein the mode field diameter range is about 30% or less, such as about 20% or less, such than about 15% or less, such as about 10% or less of the lowest mode field diameter of the range. The mode field diameter range is the range of mode field diameters corresponding to the transmission band width and the lowest mode field diameter of the range is the mode field diameter of the lowest wavelength of the transmission band width.

Advantageously the delivery fiber for at least one wavelength within said transmission bandwidth and at least along said delivery end section has a constant numerical aperture NA and a propagation loss less than 0.5 dB/m, such as less than about 0.2 dB/m, such as less than about 0.1 dB/m or even less than 0.05 dB/m.

Advantageously the delivery fiber is single mode for at least one wavelength within the transmission bandwidth. Generally the beam of light has a much higher quality for single mode light than for multimode light and for some applications single mode light is a requirement. Preferably the delivery fiber is single mode for at least about 50%, such as at least about 80% of the transmission bandwidth, such as for the entire transmission bandwidth of the delivery fiber.

In a preferred embodiment the delivery fiber is a polarization-maintaining optical fiber (PM fiber). The PM fiber may for example comprise one or more stress elements.

A PM fiber is a fiber in which linear polarization can be maintained if linearly polarized light is launched into the fiber. Advantageously the launched polarized light maintains a linear polarization during propagation along the PM delivery fiber and exits the fiber in a linear polarization state. Advantageously there is little or no cross-coupling of optical power between the two polarization modes. Preferably the PM delivery fiber is single-mode for at least one wavelength within the transmission bandwidth. By providing the delivery fiber as a PM fiber, the delivery fiber has an even lower bending loss.

The PM properties can for example be induced by incorporating stress elements e.g. such as described in U.S. Pat. No. 7,289,709.

The core region may in principle have any core diameter depending on the power and the wavelengths to be transmitted. Advantageously the delivery fiber core region has a diameter of at least about 3 µm. The core region may vary along the length of the delivery fiber, but generally it is preferred that the core region has a substantially identical diameter along the major part of the delivery fiber, such as preferably along at least about 80% of the length of the delivery fiber. The most suitable core region diameters are up to about 15 µm, such as within the range of from about 3 µm to about 10 µm, such as from about 4 µm to about 12 µm.

Where the transmission bandwidth of the delivery fiber comprises wavelengths below 500 nm or even below 450 nm, the delivery fiber core region advantageously has a diameter of less than about 10 µm because it has been found that where the core region of the delivery fiber is larger, such as larger than about 15 nm, there is an increased loss in the UV light region.

All structural details of the optical fiber, such as core region size, inclusion diameters and pattern are given in relation to a cross-sectional view of the fiber unless otherwise specified.

In an embodiment the core region diameter is substantially identical along the length of the delivery fiber, optionally excluding one or more component sections of the delivery fiber.

Such component section(s) is/are further described below.

Preferably the plurality of inclusions in the cladding region is arranged in a cross-sectional pattern comprising at least four rings of inclusions surrounding the core region, such as at least five rings of inclusions surrounding the core region. It has been found that by increasing the number of rings of inclusion the transmission bandwidth can be increased and further additional properties, such as single mode properties and/or reduced loss can be enhanced.

The rings of inclusions are advantageously arranged in a pitch pattern such that the distance between adjacent inclusions is P times the pitch, where P is 0.5 or an integer up to five, preferably up to 3, such as 1 or 2, and where P can have different value from different distances of nearest inclusions.

In an embodiment the inclusions are arranged in a pitch pattern, a double pitch pattern, a triple pitch pattern, a half pitch pattern or a combination thereof, where a pitch is determined as the smallest center to center distance between the core region and an inclusion.

It has been found that the pitch A can be used in tailoring the delivery fiber for a desired transmission band width and in particularly whether or not the transmission band width comprises wavelength in the blue range below 450 nm and/or in the red range above 800 nm. To reach into the blue wavelengths it is desired that the pitch is less than about 10 µm, preferably less than about 9 µm, such as less than about 8 µm, such as less than about 7 µm, such as less than about 6 µm. To reach into the red wavelength the pitch is advantageously about 3.2 µm or larger, such as about 3.2 µm or larger, such as about 4 µm or larger, such as about 5 µm or larger, such as about 5 µm or larger, such as about 7 µm or larger, such as about 8 µm or larger.

The core region diameter to pitch d/Λ may advantageously be about 0.7 or less, such as from about 0.3 to about 0.65, such as from about 0.4 to about 0.6.

Advantageously the core region has a refractive index $N_{core}$, the cladding region has an effective refractive index $N_{clad}$, and the refractive index $N_{bg}$ of the cladding background material is substantially identical to the refractive index of the core region $N_{core}$.

In an embodiment the refractive index of the core region is homogeneous. In another embodiment the core region is microstructured e.g., as described in co-pending DK PA 2014 00545. Where the core region is microstructured the refractive index of the core region Ncore is determined as the average refractive index.

In an alternative embodiment the refractive index $N_{bg}$ of the cladding background material differs from the refractive index of the core region $N_{core}$, preferably such that the refractive index $N_{bg}$ of the cladding background material is lower than the refractive index of the core region $N_{core}$.

In an embodiment the delivery fiber is a silica fiber and the solid inclusions are of down doped silica. Preferably the solid inclusions independently of each other are silica doped with at least one of fluorine and/or boron and/or component comprising F and/or B atoms.

The respective inclusions may have equal or different refractive indices and an inclusion may have several regions with different refractive indices in which situation the refractive index is determined as the average refractive index as described above.

In an embodiment, the difference between refractive indices of the respective inclusions independent from each other and the refractive index of the background material $N_{bg}$ is from about $10^{-5}$ to about 0.1, such as from about $10^{-4}$ to about $10^{-2}$, such as up to about $10^{-3}$.

In an embodiment the inclusions have substantially identical refractive index $N_{inc}$.

In an embodiment n of the inclusions have different refractive indices $N_{inc(1)} \ldots, N_{inc(n)}$, where n is an integer up to the number of inclusions—in other words in principle all of the inclusions may have different refractive indices. However, from a practical point of view this embodiment is not preferred.

Advantageously up to 10, such as 2-4, preferably all of the inclusions of a ring of inclusion have substantially identical refractive indices.

In an embodiment the inclusions of one ring of inclusions have a refractive index different from that of the inclusions of another ring of inclusions. Preferably the inclusions of the one ring of inclusions have higher refractive index than the inclusions of another ring of inclusions closer to the core region. By having rings of inclusions with different refractive indices, the delivery fiber can be designed to have a desired transmission bandwidth and at the same time higher order modes may be suppressed.

In an embodiment the inclusions of a ring of inclusions comprises two or more inclusions having different refractive index.

Advantageously the solid inclusions are substantially parallel to the core region. Thereby the fiber can be drawn in a relatively simple way.

In an embodiment the solid inclusions are helically surrounding the core region. Thereby the number of inclusions can be reduced and/or the bending loss can be reduced. However, the production of fiber with inclusions helically surrounding the core region is more difficult than with inclusions parallel to the core region.

In an embodiment the delivery fiber comprises an inner cladding region and an outer cladding region, where the cladding background material may differ.

In an embodiment the delivery fiber comprises an inner cladding region and an outer cladding region, where the cladding background material has identical refractive index.

In an embodiment the delivery fiber comprises an inner cladding region and an outer cladding region, where the inclusions in the outer cladding region have higher index than the inclusions in the inner cladding region. In this embodiment the inner cladding region advantageously comprises the herein described inclusions of solid material having refractive index of up to $N_{inc}$ and the inclusions in the outer cladding region are of solid material having refractive index which is higher than $N_{inc}$. Preferably the inclusions in the outer cladding region are of solid material having refractive index which is higher than the background material of the outer cladding region. Thereby the inclusions of the outer cladding region may act to couple out higher order modes.

In an embodiment the delivery fiber is a double clad delivery fiber comprising an inner cladding region and an outer cladding region for example as described above, and wherein the delivery fiber is configured such that signals can be collected e.g. via free space optic or via a coupler e.g. a fused coupler as described below.

The inclusion may in principle have any size, but generally it is desired that the inclusions are not too large unless where inclusions are used for making the fiber birefringent.

In an embodiment the solid inclusions have equal or different diameters, preferably the diameters is from about 0.2 to about 1 μm, such as from about 0.4-0.8 μm.

Preferably the inclusions of a ring of inclusions have equal diameter. In an embodiment the inclusions in a ring of inclusions have a first diameter and the inclusions in another ring of inclusions have a second diameter that differs from the first diameter.

Advantageously the delivery fiber is an all solid fiber—i.e. a fiber entirely of solid material at 25° C. Preferably the delivery fiber is an all silica fiber, wherein the core region, the cladding region and/or the inclusions are doped to reach their respective refractive indices.

In an embodiment the transmission bandwidth of the delivery fiber comprises wavelengths within the range of from about 400 nm to 900 nm. This range of wavelength is highly suitable for a plurality of high precision procedures, in particularly for microscopy based procedures. Preferably the transmission bandwidth of the delivery fiber comprises at least a bandwidth of about 100 nm, such as at least a bandwidth of about 200 nm such as at least a bandwidth of about 300 nm, such as at least a bandwidth of about 400 nm, such as the entire bandwidth within the range of from about 400 nm to 900 nm.

In an embodiment the transmission bandwidth comprises at least one wavelength in the visible range.

In an embodiment the transmission bandwidth comprises wavelengths above the visible range, for example of 700 nm or larger. This is highly suitable for illumination during eye surgery, in particular where transmission bandwidth is exclusively above 700 nm.

In an embodiment the transmission bandwidth comprises at least one wavelength below 450 nm, or even below 400 nm. Such wavelengths are very suitable for many microscopy illumination procedures.

In an embodiment the delivery fiber is configured for suppressing wavelengths above 1500 nm. This can be provided by the selection of the distance between the inclusions in the respective rings of inclusions and/or by the selection of the refractive index difference between the refractive index of the core region and the effective refractive index of the cladding region.

In an embodiment the delivery fiber is configured for suppressing wavelengths above 900 nm.

In an embodiment the transmission bandwidth of the delivery fiber comprises wavelengths within the range of from about 1100 nm to 2400 nm, preferably the transmission bandwidth of the delivery fiber comprises at least a bandwidth of about 100 nm, such as at least a bandwidth of about 200 nm such as at least a bandwidth of about 300 nm, such as at least a bandwidth of about 400 nm, such as the entire bandwidth within the range of from about 1100 nm to 2400 nm.

In an embodiment the transmission bandwidth of the delivery fiber comprises wavelengths within the range of from about 400 nm to 1100 nm.

In an embodiment the transmission bandwidth of the delivery fiber comprises wavelengths below 800 nm, such as below 700 nm, such as below 600 nm, such as below 500 nm.

The delivery fiber should not be too long because this may result in undesired bends and mechanical disturbance. However, neither should the delivery fiber be too short. In preferred embodiments the delivery fiber assembly can be supplied in different lengths for the specific use.

A suitable length of the delivery fiber is for example from about 5 cm to about 100 m, such as from about 10 cm to about 30 m, such as from about 20 cm to about 20 m, such as from about 30 cm to about 10 m.

Advantageously the delivery fiber comprises at least one component section, the component section is advantageously configured for splitting of light from the delivery fiber and/or for combining light in the delivery fiber, the component section preferably is an all fiber component section.

Advantageously the delivery fiber comprises a fused component, such as a fused coupler or a fused splitter. Such fused components are well known in the art, but have heretofore never been applied or fused to a delivery fiber. The principle of a fused element is that the core of the delivery fiber and the core of the fused component—usually a fiber component—are fused to be very close to each other so as to transfer light from one core to another. An advantage of the fused component(s) comprises an optical fiber with solid microstructures e.g. comprising a core region and a cladding region surrounding the core region wherein the cladding region comprises a cladding background material having a refractive index $TN_{bg}$ and a plurality of microstructures in the form of inclusions of solid material having refractive indices of up to $TN_{inc}$ and extending in the length of and preferably along the twin delivery fiber, wherein $TN_{inc}<TN_{bg}$ and the plurality of inclusions in the cladding region is arranged in a cross-sectional pattern comprising at least two rings of inclusions surrounding the core region.

It has been found that by using all solid fibers comprising solid microstructures in form of inclusions as described, the coupling or splitting of light to or from the delivery fiber will be such that the fraction of light coupled to or split from the delivery fiber has a substantially identical wavelength profile as the light from where it was coupled or split.

In an embodiment the delivery fiber assembly comprises a fused coupler, wherein the fused coupler is fused to the delivery fiber at the component section. Advantageously the fused coupler is a 2×2 coupler, comprising a coupling fiber fused to the delivery fiber at the component section. The coupling fiber comprises a first and a second fiber section on either side of the fused component section and is arranged such the light is coupled between the delivery fiber and the coupling fiber at the fused component section. In an embodiment the coupling fiber is arranged for coupling light into the delivery fiber and simultaneously coupling a light fraction from the delivery fiber to the coupling fiber. Such fused coupler is advantageous for use in OCT as shown in the examples below.

In an embodiment the delivery fiber assembly comprises a fused splitter, wherein the fused splitter is fused to the delivery fiber at the component section for splitting a fraction of light from the delivery fiber. Preferably the split off light fraction constitutes from 5-95% by power of the light, wherein the split off light fraction has a wavelength profile substantially identical to the light fraction from which it was split.

In an embodiment the splitter is a 10-90% ratio splitter in that the split off light will constitute about 10% by power or about 90% by power. This type of splitter is e.g. suitable for use in OCT or wafer metrology or similar apparatus.

In general the splitter can be applied for splitting any desired power fraction of light from the delivery fiber and the split off fraction can be used as a reference. In an embodiment the delivery fiber with the splitter is configured for use in an interferometer apparatus.

In an embodiment the splitter is a 50-50% ratio splitter in that the split off light will constitute about 50% by power. This embodiment may be applied for providing interleaved pulses, e.g. as described in Advanced Fluorescence Fluctuation Spectroscopy with Pulsed Interleaved Excitation, Matthias Höller, Dissertation zur Erlangung des Doktorgrades der Fakultät für Chemie and Pharmazie der Ludwig-Maximilians-Universität München, 2011.

In an embodiment the fused splitter comprises a twin delivery fiber for delivering light, the twin delivery fiber comprises a twin delivery end and a length extending from the component section to the twin delivery end and comprises along its length a core region and a cladding region surrounding the core region wherein the cladding region comprises a cladding background material having a refractive index $TN_{bg}$ and a plurality of microstructures in the form of inclusions of solid material having a refractive index of up to $TN_{inc}$ and extending in the length of and preferably along the twin delivery fiber, wherein $TN_{inc}<TN_{bg}$ and the plurality of inclusions in the cladding region is arranged in a cross-sectional pattern comprising at least two rings of inclusions surrounding the core region, preferably a twin connector member being mounted to the twin delivery fiber at a twin delivery end section of the twin delivery fiber comprising the twin delivery end.

Advantageously the delivery fiber has a transmission bandwidth of about 200 nm or more, such as of about 300 nm or more, such as of about 400 nm or more, such as of about 500 nm or more.

In an embodiment the delivery fiber assembly comprises a fused coupler and a fused splitter, wherein the fused splitter is fused to the delivery fiber at a first component section and the fused coupler is fused to the delivery fiber at a second component section closer to the delivery end of the delivery fiber, the fused splitter and fused coupler comprises a loop fiber configured for delaying a light pulse fraction split out via the splitter and recombined into the delivery fiber via the coupler such that a split off and recombined light pulse fraction is delayed relative to the light pulse fraction from which it was split.

The loop fiber is advantageously an all solid fiber comprising inclusions e.g. as described above.

Advantageously the assembly comprises an input end connector member and the input end connector member is mounted to the delivery fiber at an input end section of the delivery fiber comprising the input end, the connector member preferably being configured for connecting the input end in physical contact with a light launching unit, such as a microstructured optical fiber.

In an embodiment the assembly comprises a pre-delivery fiber, the pre-delivery fiber is coupled to the delivery fiber without free space optics.

In an embodiment the pre-delivery fiber is spliced to the delivery fiber, optionally by a splicing.

Advantageously the splicing is provided such that guiding one or more properties selected from mode field diameter, numerical aperture, low propagation loss or transmission band width are substantially unaltered from the pre-delivery fiber to the delivery fiber.

In an embodiment the delivery fiber assembly is configured for delivering light with single mode quality from a multiplum of multiplexed lasers with different wavelengths. Such multiplexed laser light is sometimes referred to as a spectral engine. The multiplexed laser light may e.g. be multiplexed from a blue, a green and a red laser which are combined into a single beam path with e.g. a Keyoptics KineFLEX module. Prior art would either be using three different delivery fibers or having a single delivery fiber which was single mode at the large wavelengths and multimode at the low wavelengths. Heretofore there has not been any solution that makes it possibly to deliver single mode multiplexed light comprising different wavelengths, such as wavelengths that differs with about 25 nm or more, such as about 100 nm or more, such as 200 nm or more, such as 300 nm or more by one single delivery fiber.

The invention also relates to a broad band source for supplying light to an apparatus. The broad band source comprises
- an optical pump source operable to generate pump pulses
- a microstructured optical fiber for generating broad band light pulses upon feeding of pump light; and
- a delivery fiber arranged for receiving at least a portion of at least some of the broad band light pulses and for delivering at least a part of the received portion of the broad band light pulses to the apparatus,
- wherein the optical pump source is arranged to launch pump pulses to the microstructured optical fiber, and the delivery fiber has a length, an input end for launching light and a delivery end for delivering light, the delivery fiber comprises along its length a core region and a cladding region surrounding the core region wherein the core region has a diameter of up to about 15 µm and the cladding region comprises a cladding background material having a refractive index $N_{bg}$ and a plurality of microstructures in the form of inclusions of solid material having a refractive index of at least $N_{inc}$ and extending in the length of and preferably along the longitudinal axis of the delivery fiber, wherein $N_{inc} < N_{bg}$ and the plurality of inclusions in the cladding region is arranged in a cross-sectional pattern comprising at least two rings of inclusions surrounding the core region.

The delivery fiber of the broad band source may advantageously be as the delivery fiber described above.

In an embodiment the delivery fiber has a transmission bandwidth of about 200 nm or more, such as of about 300 nm or more, such as of about 400 nm or more, such as of about 500 nm or more.

Advantageously, the delivery fiber has a constant mode field diameter for at least one wavelength within the transmission bandwidth at least along the delivery end section, preferably the delivery fiber has a constant mode field diameter to wavelength profile within the transmission bandwidth at least along the delivery end section. In one embodiment the delivery fiber has a substantially constant mode field diameter along its entire length including the delivery end section with the connector.

Advantageously the delivery fiber has a substantially constant mode field diameter to wavelength profile along the major part of its length, preferably as described above e.g. at least including the end sections including 1 cm from delivery end.

The delivery fiber is preferably single mode for at least one wavelength within the transmission bandwidth. Preferably the delivery fiber is single mode for at least about 50%, such as at least about 80% of the transmission bandwidth, such as for the entire transmission bandwidth of the delivery. The delivery fiber preferably has a transmission bandwidth of about 200 nm or more, such as of about 300 nm or more, such as of about 400 nm or more, such as of about 500 nm or more.

Advantageously the delivery is a polarization-maintaining optical fiber (PM fiber) as described above.

In an embodiment the plurality of inclusions in the cladding region is arranged in a cross-sectional pattern comprising at least four rings of inclusions surrounding the core region, such as at least five rings of inclusions surrounding the core region. The rings of inclusions are arranged in a pitch pattern, a double pitch pattern, a triple pitch pattern, a half pitch pattern or a combination thereof, e.g. as described above.

In an embodiment the fiber has a so called single cell core, which basically corresponds to a single missing inclusion. In this embodiment the core size is given by two times the pitch ($\Lambda$) minus the diameter of the inclusions (d).

Preferably the core region has a refractive index $N_{core}$, the cladding region has an effective refractive index $N_{clad}$, and the refractive index $N_{bg}$ of the cladding background material is substantially identical to the refractive index of the core region $N_{core}$.

The delivery fiber is advantageously a silica fiber and the solid inclusions are of down doped silica, preferably the solid inclusions independently of each other are silica doped with at least one of fluorine and/or boron and/or component comprising F and/or B atoms.

In an embodiment the delivery fiber is a double clad fiber comprising an inner cladding region and an outer cladding region, where the inclusions in the outer cladding region have higher indices than the inclusions in the inner cladding region, preferably the inner cladding region comprises the at least two rings of inclusions of solid material having a refractive index of at least $N_{inc}$ and the outer cladding region has a higher effective refractive index than the inner cladding region.

The inclusions in the outer cladding region are preferably of solid material having a refractive index which is higher than $N_{inc}$, preferably the inclusions in the outer cladding region are of solid material having a refractive index which is higher than the background material of the outer cladding region. Thereby the inclusions of the outer cladding may act to couple out higher order modes.

In an embodiment the outer cladding is arranged to receive and transmit a signal from an illuminated target. The light scattered from the target may be collimated by an optical element to be transmitted via the outer cladding e.g. to a spectrometer.

The delivery fiber is advantageously in form of a delivery fiber assembly as described above.

The optical pump source can in principle be any kind of optical pump source, e.g. such as the optical pump source described in WO 2011/023201. Advantageously the optical pump source comprises a mode-locked fiber oscillator and preferably at least one amplifier. In an embodiment the optical pump source comprises a master oscillator power amplifier MOPA. MOPA configurations are well known in the art.

The microstructured optical fiber can be any microstructured optical fiber suitable for supercontinuum generation e.g. as described in the above cited prior art documents.

Advantageously the optical pump source and the microstructured optical fiber of the broad band source are configured for generating broad band light pulses spanning at least about 200 nm, preferably at least about 500 nm, such as an octave.

Advantageously the microstructured optical fiber comprises holes which are connected to a connector member connected to the delivery fiber preferably without the use of free space optics.

In an embodiment the microstructured optical fiber comprising holes is spliced to the delivery fiber e.g. as described in US2012195554.

In an embodiment the microstructured optical fiber is connected to the delivery fiber by butt connection, optionally by connector members or by splicing, such as a cold splice or where the holes are collapsed at the end of the microstructured optical fiber.

In an embodiment the microstructured optical fiber is connected to the delivery fiber by using of a gradient index fiber arrangement (GRIN) as described in "Low-Loss High-Strength Microstructured Fiber Fusion Splices Using GRIN Fiber Lenses" by A. D. Yablon and R. Bise. 2004 Optical Society of America, OCIS codes: (060.2310) Fiber optics.

In an embodiment the broad band source comprises a band pas filter for filtering the broad band light pulses, the band pas filter is preferably a tunable band pass filter, preferably selected from a grating based filter, a prism, or an acousto-optic tunable filter (AOTF). Such band pass filters are well known to the skilled person.

Advantageously the band pass filter is positioned between the microstructured optical fiber and the delivery fiber.

In an embodiment the delivery fiber is arranged to receive the band pass filtered portion of the broad band light pulses and for delivering the at least a part of the received portion of the broad band light pulses to the apparatus without free space optics.

In an embodiment the filter is a tunable optical band pass filter, configured for selectively selecting a plurality of wavelengths or wavelength ranges and transmitting the selected wavelengths to the delivery fiber.

In an embodiment wherein the pump source is operable to generate pump pulses at a pump pulse repetition rate, and the broad band source comprises a pulse picker arranged between the pump source and the microstructured optical fiber, the pulse picker being operable to pick out pulses to reduce the pump pulse repetition rate generated by the pump source, such that the reduced pump pulse repetition rate is launched to the microstructured optical fiber.

The invention also comprises a broad band source system comprising the broad band source as described above and wherein the broad band source system comprises a plurality of delivery fiber assemblies having different transmitting properties, wherein each of the delivery fiber assemblies comprises an input end connector member and a delivery end connector member. Thereby the user can select a delivery fiber assembly for a specific use and switch to another delivery fiber assembly for another use. The respective delivery fiber assemblies are advantageously designed for the performance of different procedures and the user can relatively simply switch delivery fiber assembly.

The invention also relates to a spectral engine source for supplying light to an apparatus, the spectral engine source comprising
two or more lasers emitting laser beams with wavelength(s) that differs with at least one wavelength
a multiplexer, and
a delivery fiber Thus the spectral engine may comprise a multiplum of lasers emitting laser beams with distinct wavelength or band of wavelength.

The multiplexer is configured for receiving at least a portion of the laser beams of each of the lasers and for collimating the received light to a multiplexed beam. The delivery fiber is arranged to receive the multiplexed beam and to delivering at least a part of the received multiplexed beam to the apparatus, and wherein the delivery fiber has a length, an input end for launching light and a delivery end for delivering light. The delivery fiber comprises along its length a core region and a cladding region surrounding the core region wherein the core region has a diameter of up to about 15 μm and the cladding region comprises a cladding background material having a refractive index $N_{bg}$ and a plurality of microstructures in the form of inclusions of solid material having refractive index of up to $N_{inc}$ and extending in the length of the longitudinal axis of the delivery fiber, wherein $N_{inc}<N_{bg}$ and the plurality of inclusions in the cladding region is arranged in a cross-sectional pattern comprising at least two rings of inclusions surrounding the core region, preferably the delivery fiber has a transmission bandwidth comprising wavelengths comprising at least a part of the wavelengths of each of the two or more lasers.

The delivery fiber may be as described above.

The lasers may be any kind of lasers, such as fiber lasers or semiconductor diode lasers.

In an embodiment at least one of the laser beams emitted from the two or more lasers have a bandwidth of about 50 nm or less, such as about 25 nm or less, such as about 5 nm or less.

In an embodiment one of the laser beams emitted from the two or more lasers comprises at least one wavelength below 500 nm and one of the laser beams emitted from the two or more lasers comprises at least one wavelength above 800 nm.

In an embodiment the spectral engine comprises at least three lasers, wherein a first laser of the lasers is adapted for emitting a laser beam comprising at least one wavelength below 450 nm, a second laser of the lasers is adapted for emitting a laser beam comprising at least one wavelength in the range from 500 nm to 700 nm, and a third of the lasers is adapted for emitting a laser beam comprising at least one wavelength above 800 nm.

The invention also relates to an apparatus comprising a broad band source or a spectral engine source comprising as described above. The apparatus comprises an optical waveguide arranged for receiving light from the delivery fiber, wherein the optical waveguide comprises a connector member configured for being mated with the delivery end connector member of the delivery fiber, the optical wave guide preferably being an optical fiber.

The apparatus is for example an illumination apparatus configured for illuminating a target, the illumination apparatus is preferably selected from a microscope, a spectroscope or an endoscope.

Advantageously the illumination source is adapted for fluorescence Imaging; Fluorescence Lifetime Imaging (FLIM); Total Internal Reflection Fluorescence (TIRF) Microscopy; fluorescence resonance energy transfer (FRET); pulse interleave excitation foster resonance energy transfer (PIE-FRET); broadband Spectroscopy; nanophotonics; flow cytometry; industrial inspection, such as metrology; ringdown spectroscopy, such as gas sensing; analytical spectroscopy, such as hyperspectral spectroscopy, crop analysis e.g. of fruits and time of flight spectroscopy (TCSPC); single Molecule Imaging and/or combinations thereof. In one embodiment the delivery fiber serves as a so-called light guide in the microscope.

In an embodiment the apparatus is a metrology apparatus, the apparatus preferably comprises a double clad delivery fiber configured for collecting signals from an illuminated target.

In an embodiment the apparatus comprises at least one delivery fiber assembly comprising a fused coupler and/or at least one delivery fiber assembly comprising a fused splitter.

In an embodiment the illumination source comprises at least one delivery fiber assembly comprising a fused coupler and/or at least one delivery fiber assembly comprising a fused splitter and wherein the delivery fiber has a transmission bandwidth of at least about 200 nm, preferably at least about 500 nm, such as an octave.

All features of the inventions and embodiments of the invention as described above including ranges and preferred ranges can be combined in various ways within the scope of the invention, unless there are specific reasons not to combine such features.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings.

FIG. 1a shows a cross-section of a delivery fiber of an embodiment of a delivery fiber assembly of the invention.

FIG. 1b shows a wavelength profile in form of a transmission loss spectrum for a delivery fiber as shown in FIG. 1a.

FIG. 1c shows an example of a PM fiber, where the dark regions are inclusions doped with another material, such as e.g. boron FIG. 1d shows an example of the long wavelength transmission edge and short wavelength transmission edge versus the pitch for a fiber according to the invention.

FIG. 11 is an illustration of another apparatus of an embodiment of the invention The figures are schematic and may be simplified for clarity. Throughout, the same reference numerals are used for identical or corresponding parts.

FIG. 1a shows a cross-section of a delivery fiber 5 of a delivery fiber assembly. The delivery fiber 5 comprises a core region with a refractive index $n_{core}$. The core is surrounded by a cladding region comprising a background material having a refractive index $N_{bg}$ and a plurality of microstructures in the form of inclusions 2a, 2b of solid material having refractive index up to $N_{inc}$ and extending in the length of the longitudinal axis of the delivery fiber, wherein $N_{inc} < N_{bg}$. The plurality of inclusions 2a, 2b in the cladding region is arranged in a cross-sectional pattern comprising at least 6 rings of inclusions surrounding the core region. In the shown embodiment, the 3 in radial direction innermost rings of inclusions 2a have a lower refractive index than the 3 in radial direction outermost rings of inclusions 2b. In the shown embodiments the inclusions have substantially equal diameter. As explained above it may for some applications be advantageous to have different diameters for one ring of inclusions relative to another ring of inclusions.

FIG. 1b shows a transmission loss spectrum of a fiber corresponding to the delivery fiber shown in FIG. 1 with six rings of inclusions, but where all inclusions have same refractive index. In this example the core has a diameter of 10 μm, the inclusions have a refractive index which is 1.2% lower than the refractive index of the core and the cladding background silica material at 635 nm. The center to center distance between the inclusions in the cladding (also known as the pitch) is 6 μm and the diameter of the inclusions is 3 μm.

Figure 2:
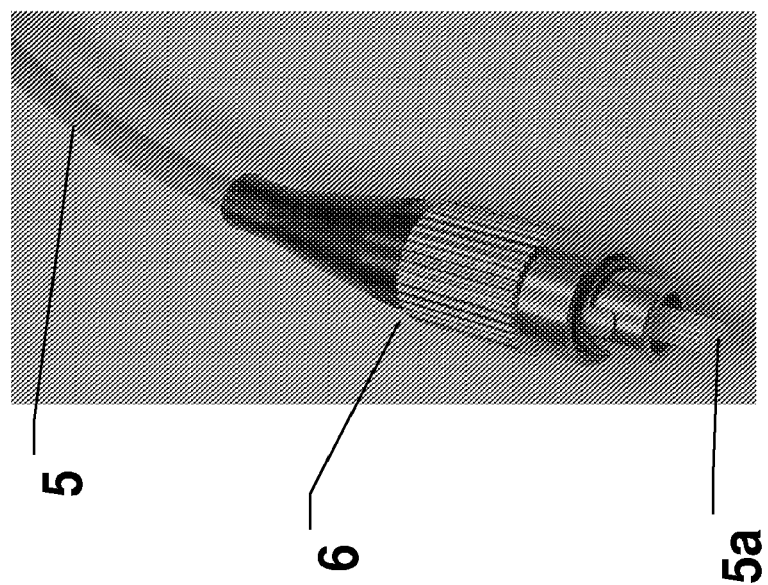
FIG. 2 shows a perspective view of a part of an embodiment of the delivery fiber assembly of the invention.

The spectrum is obtained by sending light from a broad band spectrum light source through the fiber and performing a cut-back to separate the coupling loss. The peak at around 1400 nm is due to water absorption. The delivery fiber is single-mode in the entire transmission bandwidth of the delivery fiber. It can be seen that the delivery fiber has a very broad transmission bandwidth extending from about 425 nm to about 1500 nm.

The delivery fiber shown in FIG. 1c is an example of a PM fiber comprising a core region with a refractive index $n_{core}$. The core is surrounded by a cladding region comprising a background material having a refractive index $N_{bg}$ and a plurality of microstructures in the form of inclusions 7a, 8b of solid material having refractive index up to $N_{inc}$ and extending in the length of the longitudinal axis of the delivery fiber, wherein $N_{inc} < N_{bg}$. The plurality of inclusions 7a, 7b in the cladding region is arranged in a cross-sectional pattern comprising at least 6 rings of inclusions surrounding the core region. In the shown embodiment, a number of inclusions b with a higher refractive index than the other inclusions 7a is arranged in two opposite clusters for forming stress elements. The inclusions 7b with the higher refractive index are e.g. doped with boron.

In an embodiment of the of the delivery fiber is has been found that the diameter (d) of the inclusions in the cladding relative to the pitch ($\Lambda$) may have large influence on the guiding properties of the delivery fiber. In an embodiment the transmission loss is large if the d/$\Lambda$ is less than about 0.4. In an embodiment the fiber is multimode if d/$\Lambda$ is more than about 0.6.

In an embodiment of the invention is has been found that the pitch ($\Lambda$) of the delivery fiber may have large influence on the spectral transmission bandwidth of the delivery fiber.

In particular it was found that the short wavelength transmission edge sets a upper limit to the pitch and where this limit increases with the required short wavelength edge, such that e.g. a short wavelength edge of 300 nm requires a pitch of less than 6 μm whereas a short wavelength edge of 600 nm requires a pitch of less than 9 μm.

Further it was found that the long wavelength transmission edge sets a lower limit to the pitch and where this limit increases with the required long wavelength edge, such that e.g. a long wavelength edge of 800 nm requires a pitch of at least 3.2 μm whereas a long wavelength edge of 1500 nm requires a pitch of at least 6 μm.

FIG. 1d shows the pitch shows an example of the long wavelength transmission edge (201) and short wavelength transmission edge (202) versus the pitch for a fiber according to the invention having a d/Λ of about 0.5.

In an example the mode field diameter of the delivery fiber varies from about 8.0 μm at 500 nm to about 9.0 μm at 900 nm. In an embodiment the mode filed diameter of the fiber varies by less than about 20% from 500 nm to 900 nm.

FIG. 2 shows a part of a delivery fiber assembly comprising the delivery fiber 5 and a connector member 6 mounted to the delivery fiber at a delivery end section of the delivery fiber comprising the delivery end 5a. As it can be seen the delivery fiber comprises a protection coating, such as a polymer protection coating.

The connector member is advantageously an optical fiber connector of the type which in the prior art is commonly used to terminate the end of an optical standard fiber to enable easy connection and disconnection of two standard optical fibers with low loss.

During mounting, the optical fiber is typically aligned inside the optical connector member, so that the core region of the optical delivery fiber is centered inside a connector plane of the connector member. For a polarizing or polarization maintaining fiber it is also possible to rotate the fiber so that the polarization axis is in a predetermined plane. Furthermore it is ensured that the end facet of the fiber is in the output plane of the connector member. This can e.g. be achieved by polishing the connector and fiber end facets.

If light is sent through the delivery fiber assembly with a connector member on the output end, then the position of the light being emitted from the output of the connector member is well known. For a standard all-solid single mode fiber the light will have its focal plane and thereby waist at the output plane of the connector.

Many different types of connectors have been introduced to the marked, such as e.g. FC, E-2000, SMA connectors, as well as connectors with built in beam expansion.

It is desired to use fiber connector members having low loss and high power handling, as they should advantageously be capable of handling average powers such as up to 100 mW or even up to several Watts.

Figure 3:
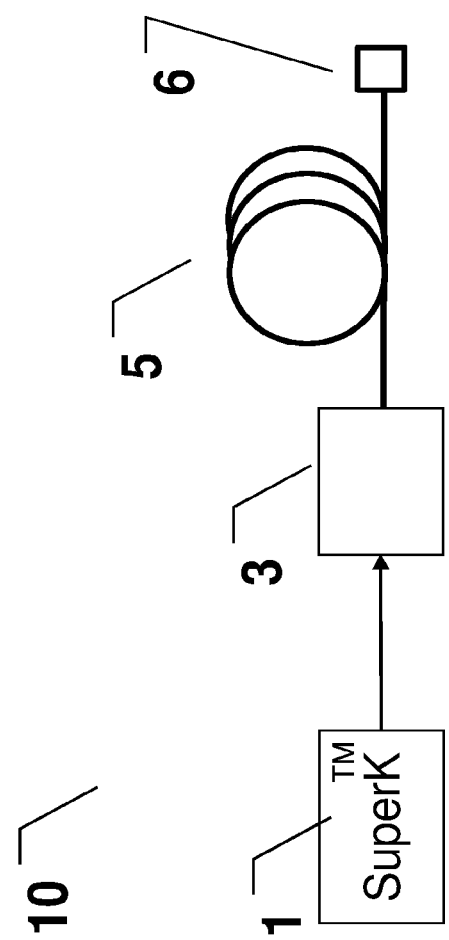
FIG. 3 is a schematic illustration of an embodiment of a broad band source of the invention.

The broad band source 10 shown in FIG. 3 comprises a broad band laser pulse generator 1 comprising a not shown optical pump source operable to generate pump pulses and a not shown microstructured optical fiber for generating broad band light pulses upon feeding of pump light where the optical pump source is arranged to launch pump pulses to the microstructured optical fiber. In the shown embodiment the broad band laser pulse generator 1 is in the form of a SuperK™ system marketed by NKT Photonics Denmark. The broad band source further comprises a delivery fiber 5 comprising solid inclusions as described above. The delivery fiber 5 is arranged for receiving at least a portion of at least some of said broad band light pulses. In the shown embodiment the broad band source 10 further comprises an optical component 3, preferably a filter 3 arranged between the broad band laser pulse generator 1 and the delivery fiber 5. The optical component 3 is for example a polarizer, a spectral filter (preferably tunable) and/or a beam splitter.

At the output end section of the delivery fiber 5, the delivery fiber comprises a connector member 6 e.g. as described above. The connector member 6 is advantageously configured for delivering at least a part of said received portion of said broad band light pulses to an apparatus as described above.

Figure 4:
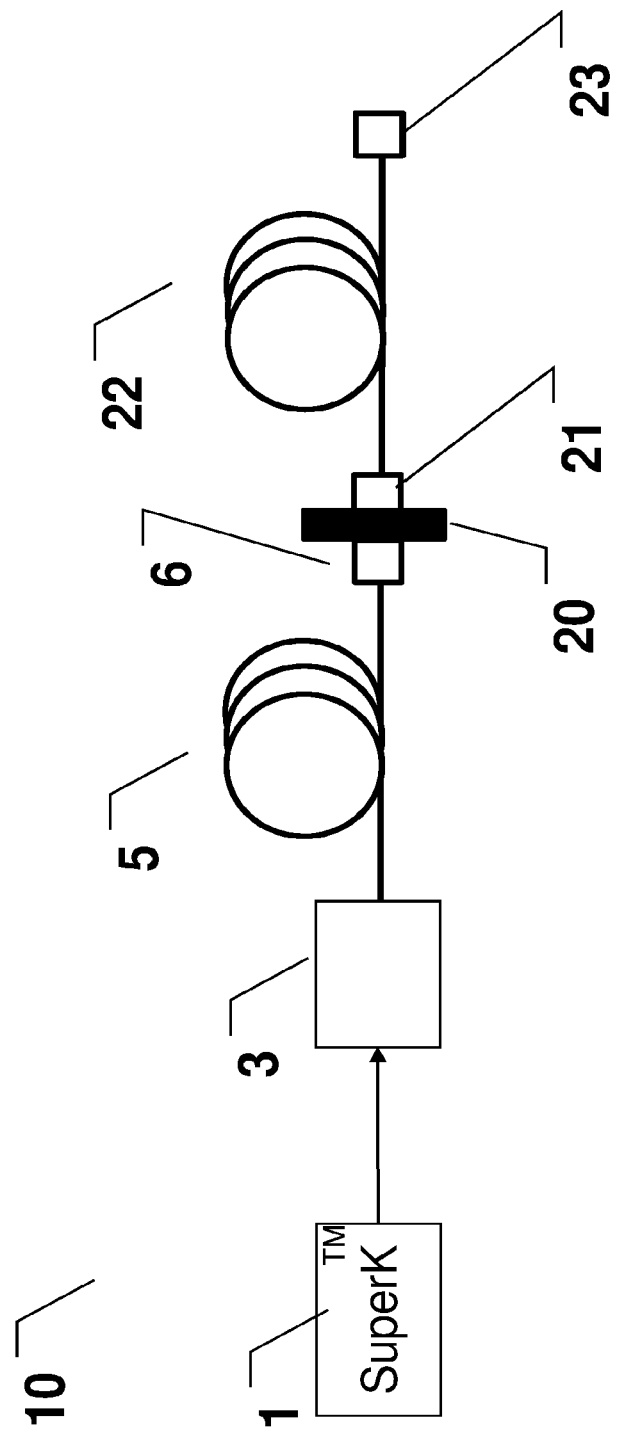
FIG. 4 is a schematic illustration of another embodiment of a broad band source of the invention.

In the embodiment shown in FIG. 4 the broad band source 10 is coupled to an optical waveguide arranged for receiving light from the delivery fiber, here called the first delivery fiber. In this embodiment the optical waveguide arranged for receiving light from the first delivery fiber is in form of an additional delivery assembly comprising a second delivery optical fiber 22 and a second delivery fiber inlet end connector member 21 and a second delivery fiber output end termination unit 23. The connector member 6 of the delivery fiber assembly 5, 6 in the following referred to as the first delivery fiber assembly 5,6 is connected to the second delivery fiber inlet end connector member 21 using a mating sleeve 20.

By using a mating sleeve the connectors mechanically couple the core regions of the first and the second delivery fibers 5, 22 so that light can pass from the first delivery fiber 5 to the second delivery fiber 22 with low loss. Preferably the connector members are spring-loaded, so the fiber faces are pressed together when the connector members 6, 21 are mated. The resulting glass-to-glass or plastic-to-plastic contact eliminates signal losses that would be caused by an air gap between the joined fibers.

The fiber termination unit 23 is advantageously a connector member, a collimator, a ball lens, grin lens or any other suitable termination unit.

The second optical delivery fiber 22 can in principle be any kind of optical fiber, preferably having a relative broad transmission bandwidth e.g. at least about 200 nm or more, and preferably the transmission bandwidth of the second optical delivery fiber 22 at least partially overlaps the transmission bandwidth of the first delivery fiber 5.

In an embodiment the second optical delivery fiber 22 is substantially identical to the first delivery fiber 5.

In an embodiment the broad band source 10 comprising the broad band laser pulse generator 1 and the first fiber delivery assembly 5,6 can be replaced without replacing the second fiber delivery assembly 21, 22, 23 or vice versa.

In an embodiment the broad band source 10 and said second fiber delivery assembly 21, 22, 23 is built into an apparatus or alternatively the second fiber delivery assembly 21, 22, 23 is built into an apparatus while the broad band source 10 is arranged to feed light to the apparatus via the connection between the connector members 6, 21. Examples of such apparatus are microscopes, bio-imaging systems (such as e.g. OCT, SLO, STED, CARS and photoacoustic systems), alignment or overlay system and manufacturing equipment (such as e.g. semiconductor manufacturing equipment). This embodiment of the invention enables that the broad band source 10 easily can be disconnected for service and/or can be replaced independently of said second fiber assembly 21, 22, 23, which e.g. may be more difficult to disconnect from the remainder of the apparatus. For example the supercontinuum source and first fiber delivery assemble constituting a broad band source of an embodiment of the invention can be comprised in a first module, whereas the second fiber assembly 21, 22, 23 is part of a second module such as e.g. an alignment sensor in a semiconductor wafer scribing system. In this example the invention enables a modular build-up of the semiconductor wafer scribing system. If the semiconductor wafer scribing system breaks down, then the error can be located to the specific module which has failed, and this can be replaced independently of the other modules. This improves risk management for the semiconductor wafer scribing system compared to having to replace both modules at the same time.

In an embodiment the second fiber delivery assembly 21, 22, 23 is used in bio-medical imaging or surgical applications. Examples of such embodiments include endoscopy, colonoscopy, rhinoscopy and bronoscopy as well as other applications where a part of the second optical fiber enters inside either a human or animal body. In such embodiments the broad band source 10 as shown in FIG. 3 can easily be connected to the connection member 21 as described above.

In an embodiment the second fiber delivery assembly is sterilized before use.

In an embodiment the second fiber delivery assembly is disposable.

Figure 5:
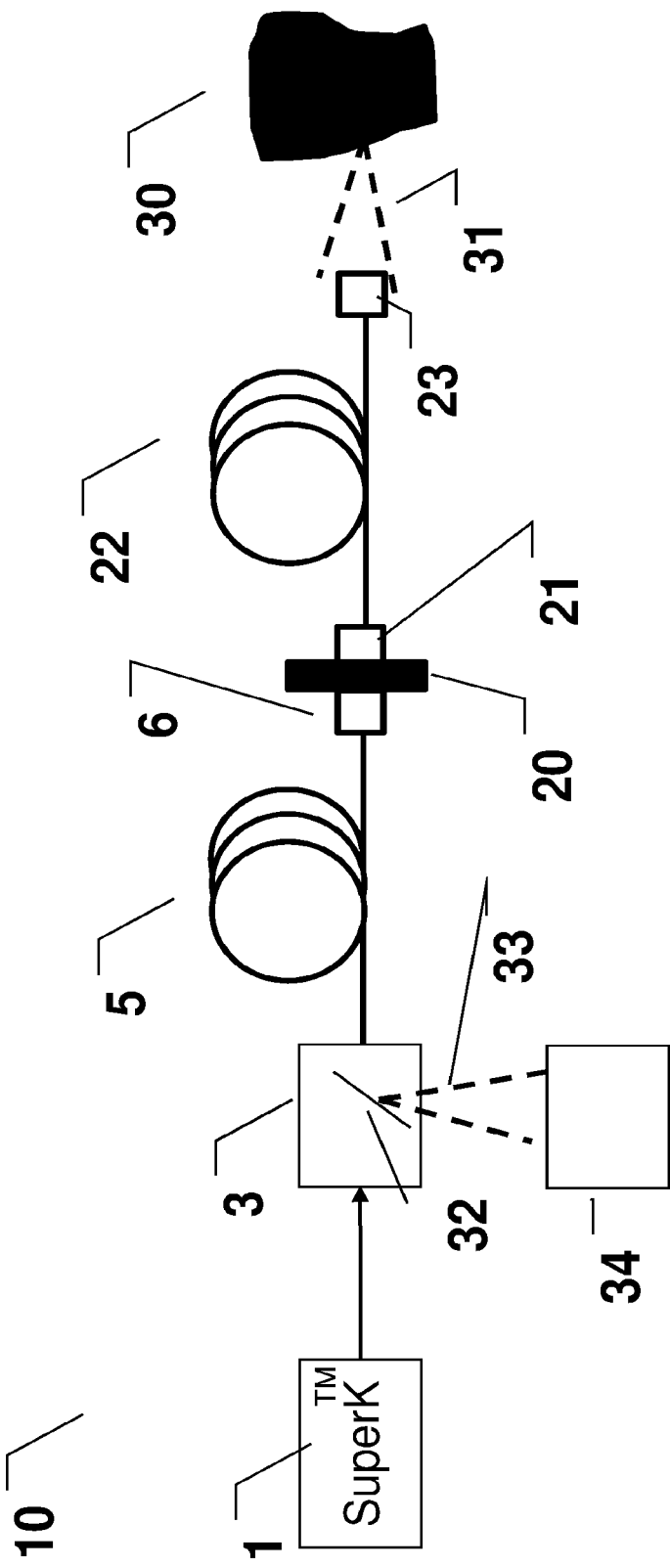
FIG. 5 is a schematic illustration of yet another embodiment of a broad band source of the invention.

FIG. 5 is a schematic illustration of another embodiment of a broad band source of the invention. The broad band system 10 may be as described above and the second optical delivery fiber assembly 21, 22, 23 may be as described in FIG. 4.

The fiber termination unit 23 advantageously is or comprises a collimator for focusing light towards a sample 30.

Advantageously the second fiber delivery assembly 21, 22, 23 is built into an apparatus and the broad band source 10 is optionally arranged as a built in module in the apparatus and is arranged to feed light to the apparatus via the connection between the connector members 6, 21. The source 10 comprises or is optically connected to an optical detector 34, and the optical component 3 comprises an additional filter 32 arranged to direct a portion of light 33 reflected by the sample and guided by the fibers 5 and 22. The additional filter is advantageously a splitter.

In an embodiment the delivery fiber 5 and the second optical fiber 22 are double clad fibers. Thereby a portion of the light 31 reflected by the sample can be guided to the optical detector via the second optical delivery fiber assembly 21, 22, 23 and the first delivery fiber assembly 5, 6. In an embodiment the delivery fiber 5 and the second optical fiber 22 comprise a cladding with an NA of at least 0.1, such as at least 0.15, such as at least 0.22. Also in this embodiment the fibers 5, 22 will guide some of the light 31 which is being reflected from the sample under test.

In an embodiment the optical component 3 comprises means to separate the light that is reflected from the sample and guided by the fibers 33 from at least some of the light from the broad band source. Such means is for example a beam splitter 32.

In an alternative embodiment a double-clad fiber coupler is applied instead of a splitter for example by providing a double-clad fiber coupler at the input end of the first delivery fiber. The double-clad fiber coupler is advantageously configured for separating core and cladding light, e.g. by having a 2×2 port structure comprising multimode double clad fibers on two ports of the coupler and single mode double clad fibers on the other two ports, such as e.g. the DC1300 LEB offered by Thorlabs. In principle a portion or all of the reflected light could be separated from the major part of the light from the broad band source but any other means known to the skilled person.

Advantageously the reflected and separated light is transmitted to an optical detector 34, such as e.g. a photodiode or a spectrometer.

Figure 6:
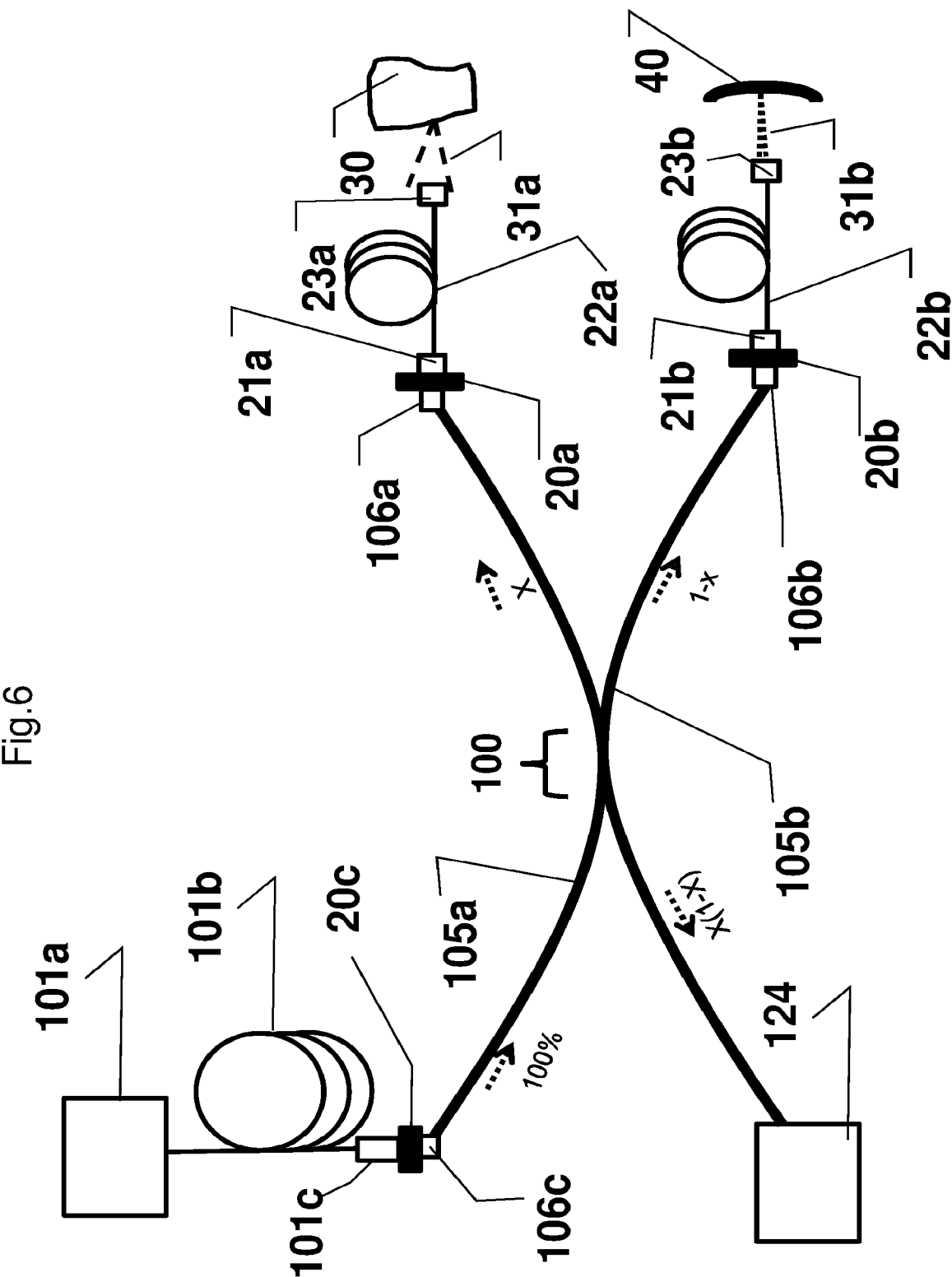
FIG. 6 is a schematic illustration of an embodiment of an apparatus of the invention in form of an interferometer.

FIG. 6 is a schematic illustration of an embodiment of an apparatus of the invention in form of an interferometer e.g. for use in optical coherence tomography (OCT) e.g. for visualization of internal tissue. The interferometer comprises a first delivery fiber assembly 105a, 106a comprising a fused coupler delivery fiber assembly 105b, 106b where the first delivery fiber assembly 105a, 106a and the fused coupler delivery fiber assembly 106b is fused in a component section 100. The interferometer comprises a broad band source comprising an optical pump source 101a operable to generate pump pulses an air hole microstructured optical fiber 101b for generating broad band light pulses upon feeding of pump pulses from said optical pump source 101a and the first delivery fiber assembly 105a, 106a comprising a delivery fiber 105a comprising solid inclusions as described above and a connector member 106a also as described above. The first delivery fiber assembly 105a, 106a is connected to the microstructured optical fiber via a delivery fiber connector member 106c which is advantageously as the connector member described above, and an end cap connection member 101c. In the end cap connection member 101c the air holes along less than a few mm of the air hole microstructured optical fiber 101b are collapsed and the light beam is collimated by a not shown lens. The delivery fiber connector member 106c and the end cap connection member 101c are mated and held together by a mating sleeve 20c. In an alternative embodiment the air hole microstructured optical fiber 101b is spliced to the delivery fiber 105 by splicing and/or by using a using a GRIN lens as described above.

The interferometer comprises a second fiber assembly 21a, 22a, 23a which advantageously is as the second fiber assembly 21, 22, 23 described above, and the connector members 106a, 21a are connected and hold together by mating sleeve 20a.

The fused coupler delivery fiber assembly 105b, 106b is connected to a third fiber assembly 21b, 22b, 23b which advantageously is as the second fiber assembly 21, 22, 23 described above, and the connector members 106b, 21b are connected and held together by mating sleeve 20b. The interferometer further comprises a mirror 40 or another reference unit arranged to reflect light emitted via the fiber termination unit 23b. In an alternative embodiment the reference unit is not included in the apparatus but can be selected by the user.

The fused coupler delivery fiber assembly 105b is further connected to a detector 124, such as a spectrometer. The broad band source may comprise one or more tunable or non-tunable filters and or a pulse picker and one or more amplifiers such as it is well known in the art.

In general a coupler has a bar port, where the light goes straight through from one top arm to the other top arm (or from the bottom arm to the other bottom arm), and a cross port where the light goes from the top arm to bottom arm, or vice versa. Often couplers are close to have a very low loss such that all the light is send to the bar port or the cross port. In this embodiment the two top arms are provided by the delivery fiber 105a on either side of the component section 100 and the bottom arms are provided by the delivery fiber 105b on either side of the component section. The bar ports and the cross port are provided by the component section 100. The bar port has a transmission coefficient of x and the cross arm a transmission coefficient of (1−x). The transmission coefficient is the same irrespective of which direction the coupler is traversed.

In use broad band light pulses are transmitted to the delivery fiber 105a and as marked on the illustration in the end of the delivery fiber 105a nearest to the microstructured optical fiber the light pulses power is set to be 100%="1". At the fused component section 100, some of the light (x) is transmitted further via the delivery fiber 105a and some of the light (1−x) is transmitted further via the fused coupler delivery fiber 105b.

The light portion (X) transmitted from the fused component section 100 and via the delivery fiber 105a is transmitted to the second fiber assembly 21a, 22a, 23a and via the fiber termination unit 23a the light pulses are emitted towards a sample 30 and reflected light 31a is transmitted in the opposite direction via the second fiber 22a and the delivery fiber 105a until the remitted light reaches the fused component section 100. From there a portion of remitted light is transmitted further via the fused coupler delivery fiber 105b to the detector 104.

The light portion (1−X) transmitted from the fused component section 100 and via the fused coupler delivery fiber 105b is transmitted to the third fiber assembly 21b, 22b, 23b and via the fiber termination unit 23b the light pulses are emitted towards a mirror 40 and reflected light 31b is transmitted in the opposite direction via the third fiber 22b and the fused coupler delivery fiber 105b until the remitted light reaches the fused component section 100. From there a portion of remitted light is transmitted further via the fused coupler delivery fiber 105b to the detector 104. Advantageously the mirror reflects substantially all of the light that is incident on it.

As explained the interferometer thereby has two interferometer arms, one that is guiding light to a sample and re-transmit reflected light and one that is guiding light to a reference unit (e.g. a mirror) and re-transmits reflected light. In an embodiment one interferometer arm is configured for being focused onto a tissue sample and for scanning the sample in an X-Y longitudinal raster pattern. The other interferometer arm is bounced off the reference mirror. Reflected light from the tissue sample is combined with reflected light from the reference.

As mentioned above in the embodiment shown in FIG. 6 the light goes from the broad band laser goes through the cross port of the coupler to reach the mirror 40. It is reflected from the mirror and goes back through the bar port of the coupler to reach the detector 124. Assuming that the reflection is loss less the transmission coefficient for the entire path is the product of the two transmission coefficients, i.e. x(1−x).

Figure 7:
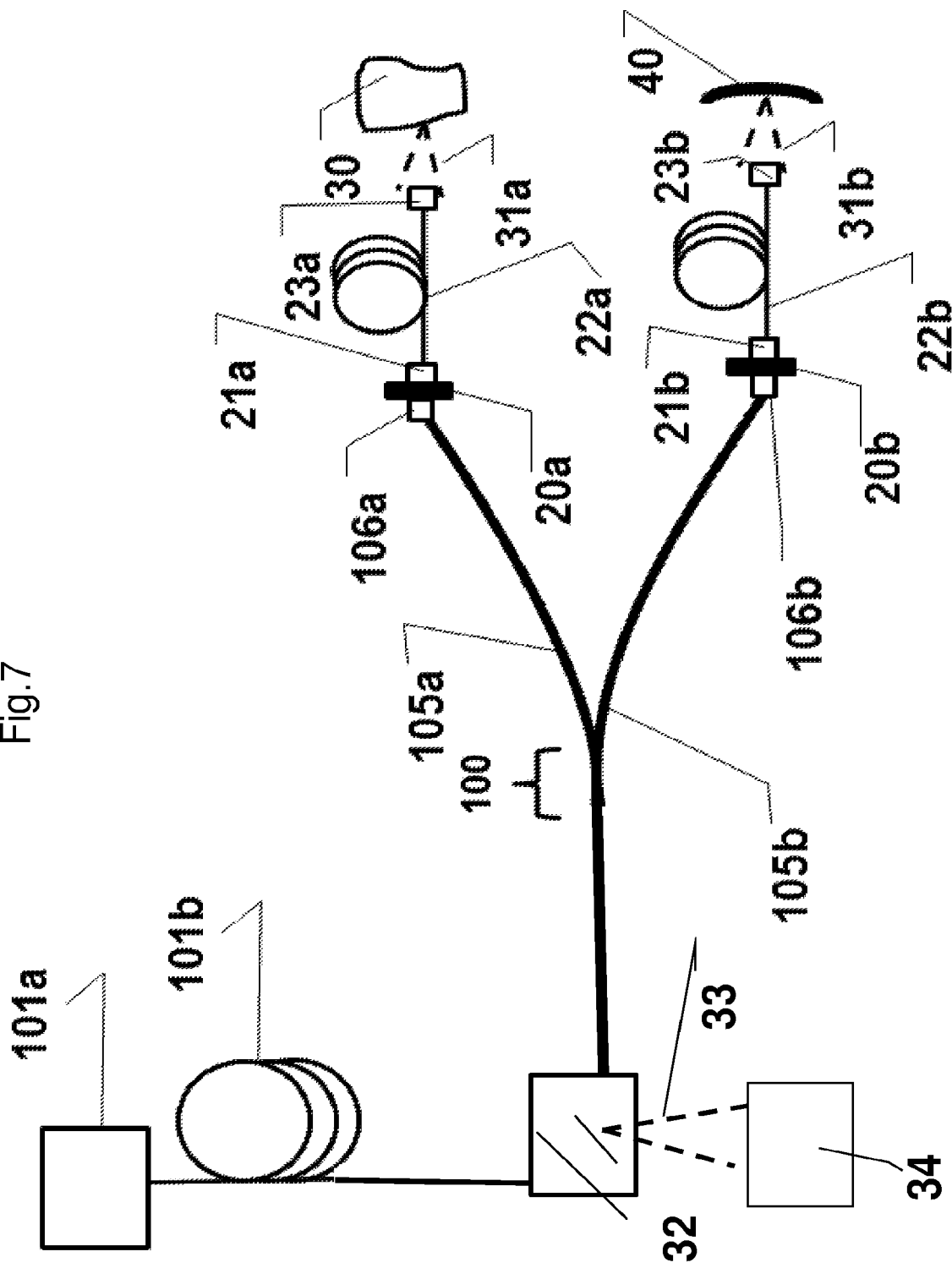
FIG. 7 is a schematic illustration of an embodiment of an apparatus of the invention in form of another type of interferometer.

FIG. 7 is a schematic illustration of an embodiment of a delivery fiber of the invention comprising a combiner.

Advantageously all of the delivery fibers 105a, 105b, 22a, 22b are all solid fibers comprising microstructures in form of inclusions as described above and preferably all of the delivery fibers 105a, 105b, 22a, 22b have a transmission bandwidth of 200 nm or more, preferably the transmission bandwidths are overlapping or identical.

FIG. 7 is a schematic illustration of an embodiment of an apparatus of the invention in form of another type of interferometer e.g. for use in optical metrology e.g. for thin film, wafer, optical critical dimension (OCD), overlay and wafer stress for transistor and interconnect metrology applications.

Parts of the interferometer of FIG. 7 are similar to corresponding parts of the interferometer of FIG. 6. The interferometer comprises a first delivery fiber assembly 105a, 106a comprising a fused splitter delivery fiber assembly 105b, 106b where the first delivery fiber assembly 105a, 106a and the fused splitter delivery fiber assembly 106b is fused in a component section 100. The interferometer comprises a broad band source comprising an optical pump source 101a operable to generate pump pulse, a microstructured optical fiber 101b for generating broad band light pulses upon feeding of pump pulses from said optical pump source 101a and the first delivery fiber assembly 105a, 106a comprising a delivery fiber 105a comprising solid inclusions as described above and a connector member 106a also as described above. The first delivery fiber assembly 105a, 106a is connected to the microstructured optical fiber via a filter 32 arranged to directing a portion of reflected light 33 reflected by the sample 30e and the reference unit 40 towards an optical detector 34. The remaining parts are as in the example of FIG. 7.

Figure 8:
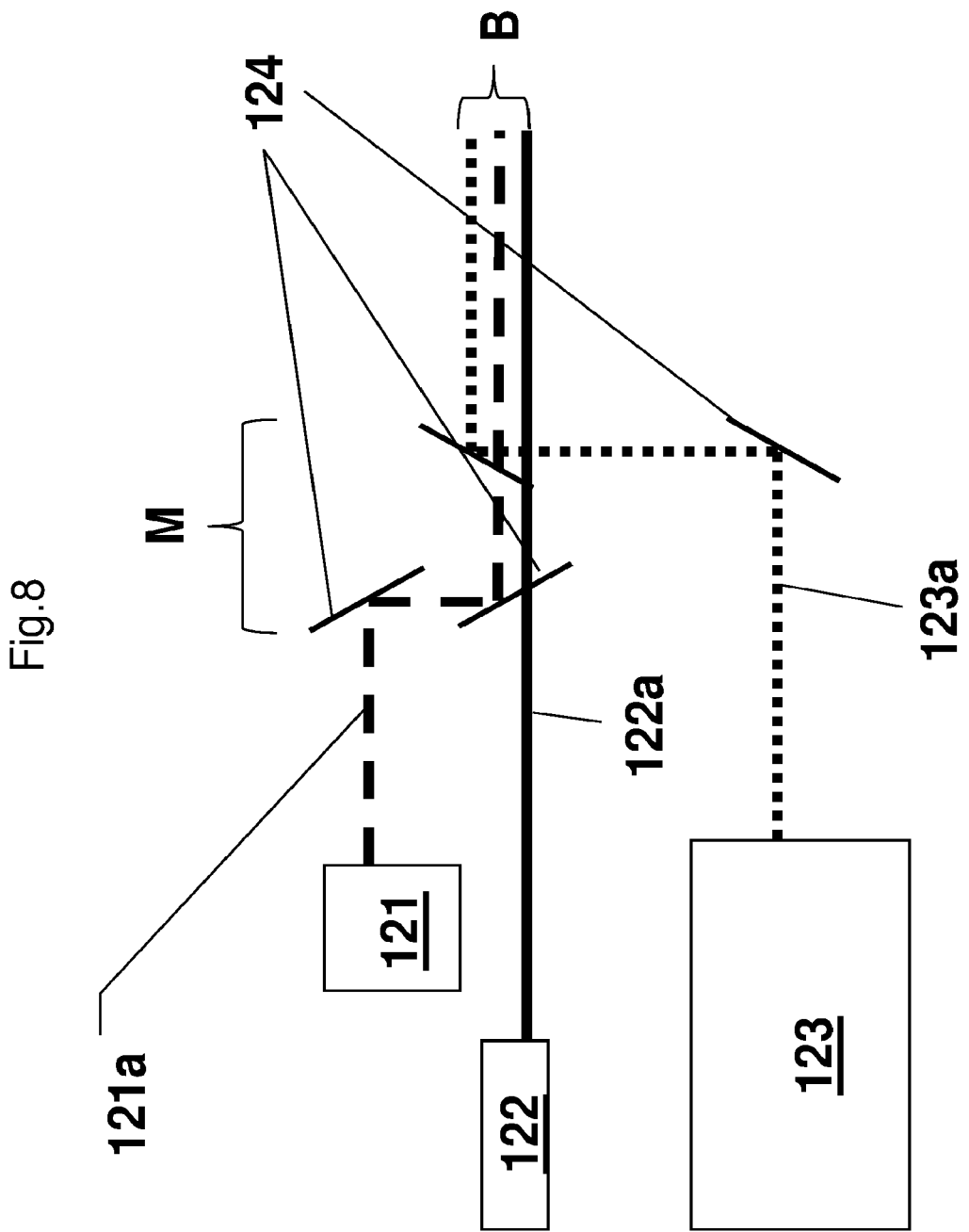
FIG. 8 is a schematic illustration of an embodiment of a spectral engine source of the invention.

FIG. 8 illustrates a spectral engine source suitably for supplying light to an apparatus. The spectral engine source comprises three lasers 121, 222, 123 emitting laser beams 121a, 122a, 123a respectively. The laser beams 121a, 122a, 123a differs from each other with at least one wavelength as described above.

The lasers 121, 222, 123 may be of same or of different types, such as one or more gas lasers, one or more chemical lasers, one or more metal-vapor lasers and/or one or more semiconductor lasers.

Figure 9:
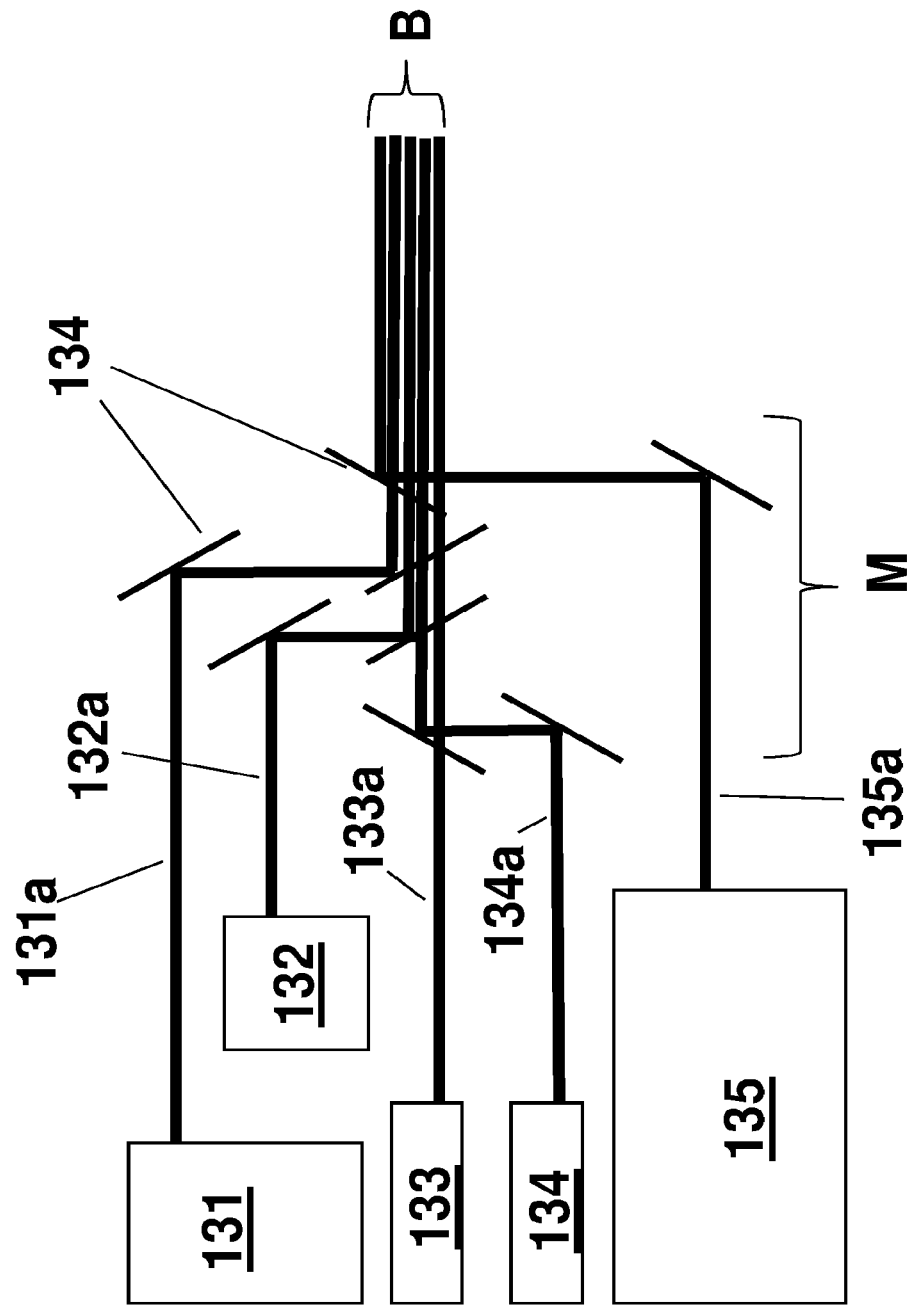
FIG. 9 is a schematic illustration of another embodiment of a spectral engine source of the invention.

The spectral engine source further comprises a multiplexer M here illustrated by a number of mirrors arranged to combine the beams 121a, 122a, 123a into one single multiplexed beam M. It should be understood that the multiplexer may be any kind of multiplexer or combiner capable of combining least a portion of the laser beams of each of the lasers and for collimating the received light to a multiplexed beam. The multiplexer M collimates the 121a, 122a, 123a sufficiently close to be received by the delivery fiber of the spectral engine source of the invention. For simplification the delivery fiber is not shown of the spectral engine source, however the delivery fiber is arranged to collect the multiplexed beam M and to delivering at least a part of the received multiplexed beam M to the apparatus, FIG. 9 illustrates another spectral engine source suitably for supplying light to an apparatus. The spectral engine source comprises 5 lasers 131, 232, 133, 134, 135 emitting laser beams 131a, 132a, 133a, 134a, 135a respectively. The laser beams 131a, 132a, 133a, 134a, 135a differs from each other with at least one wavelength. For example laser beam 131a may comprise wavelength (s) in the range of 400-500 nm, laser beam 132a may comprise wavelength (s) in the range of 500-600 nm, laser beam 133a may comprise wavelength (s) in the range of 600-700 nm, laser beam 135a may comprise wavelength (s) in the range of 800-900 nm.

Figure 10:
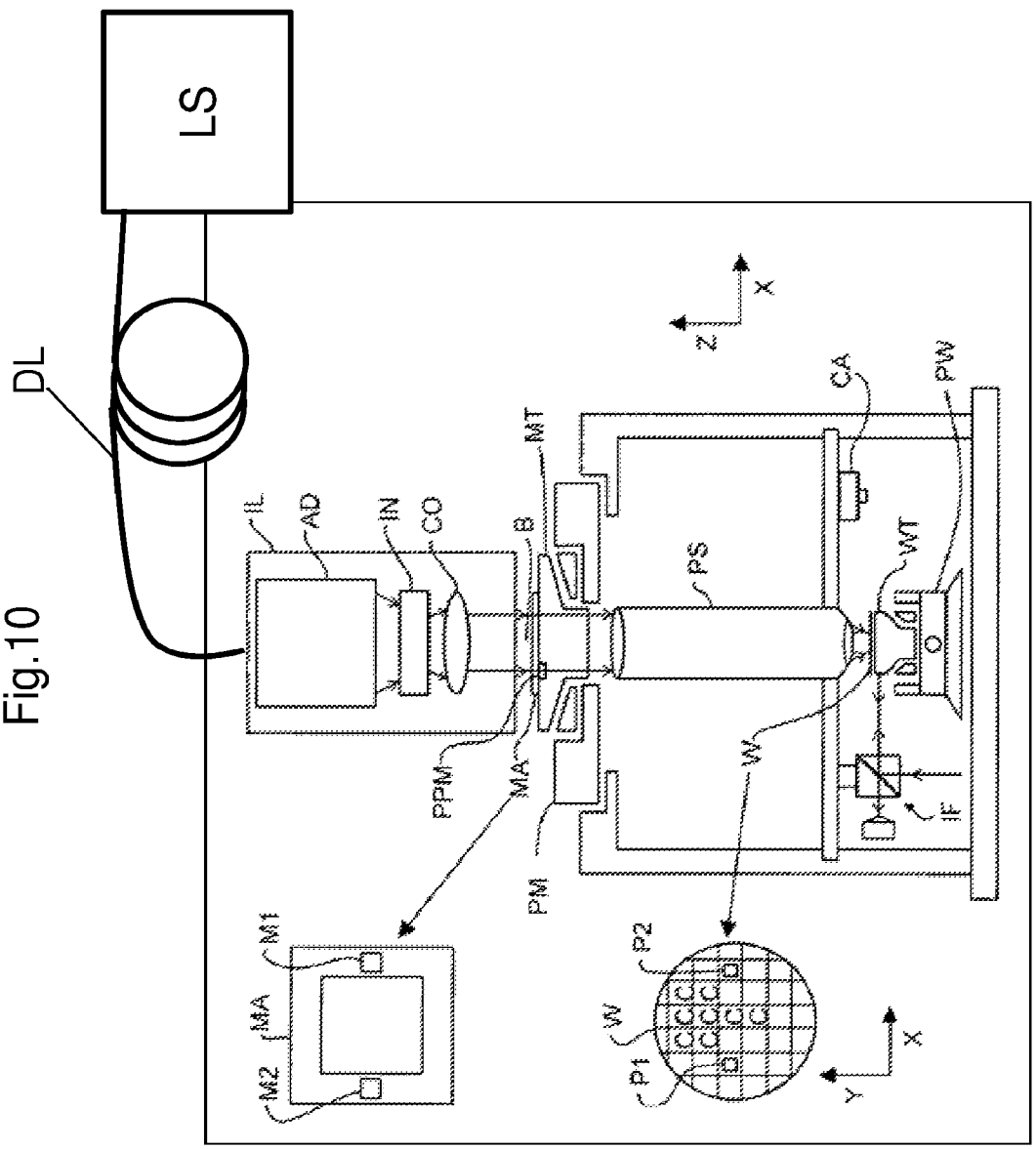
FIG. 10 is an illustration of an apparatus of an embodiment of the invention

The spectral engine source further comprises a multiplexer M here illustrated by a number of mirrors arranged to combine the beams 131a, 132a, 133a, 134a, 135a into one single multiplexed beam M. The spectral engine source also comprises a not shown delivery fiber as described above for receiving the multiplexed beam and to delivering at least a part of the received multiplexed beam M to an apparatus, FIG. 10 illustrates an apparatus of an embodiment of the invention comprising a light source LS selected from a broad band source, a broad band source system or a spectral engine source with a delivery fiber DL as described above. The apparatus is a lithographic apparatus and comprises an illumination system (illuminator) IL arranged to receive the light from the delivery fiber of the light source LS. The illuminator IL may comprise an adjuster AD for adjusting the angular intensity distribution of the radiation beam received from the light source LS. In addition, the illuminator IL may comprise various other components, such as an integrator IN and a condenser CO. The illuminator may be used to condition the radiation bean, to have a desired uniformity and intensity distribution in its cross-section.

The radiation beam B is incident on a patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies. The apparatus may for example operate as described in US2007013921

FIG. 11 illustrates an apparatus of an embodiment of the invention comprising scanning microscope that is embodied as a confocal scanning microscope and a light source LS selected from a broad band source, a broad band source system or a spectral engine source with a delivery fiber DL as described above. The light source LS delivers an illuminating light beam 211 via the delivery fiber DL The scanning microscope comprises an acoustooptical component 213 that is embodied as AOTF 215. From acoustooptical component 213, light 212, selected out of illuminating light beam 211, arrives at a beam deflection device 17 that contains a gimbal-mounted scanning mirror 19 and that guides illuminating light beam 211 through scanning optical system 221, tube optical system 223, and objective 225 over or through specimen 227. Detected light beam 229 coming from the specimen travels in the opposite direction through scanning optical system 221, tube optical system 223, and objective 225, and arrives via scanning mirror 219 at acoustooptical component 213 which conveys detected light beam 229 to detector 231, which is embodied as a multi-band detector. Illuminating light beam 211 is depicted as a solid line in the drawing, and detected light beam 229 as a dashed line. Illumination pinhole 233 and detection pinhole 235 that are usually provided in a confocal scanning microscope are schematically drawn in for the sake of completeness. Omitted in the interest of better clarity, however, are certain optical elements for guiding and shaping the light beam.

Acoustooptical component 213, which serves to select the wavelength spectrum that is chosen, is configured as AOTF 215, through which an acoustic wave passes. The acoustic wave is generated by an electrically activated piezo acoustic generator 237. Activation is accomplished by a high-frequency source 239 that generates an electromagnetic high-frequency wave that exhibits an adjustable HF spectrum. The HF spectrum is chosen in such a way that only those portions of illuminating light beam 211 having the desired wavelength arrive at beam deflection device 217. The other portions of illuminating light beam 211 not influenced by the acoustic excitation are directed into a beam trap 241. The power level of the illuminating light beam 211 can be selected by varying the amplitude of the acoustic wave. The crystal sectioning and orientation of acoustooptical component 213 are selected in such a way that with a single coupling-in direction, different wavelengths are deflected in the same direction. A computer 243 is used to choose a second or third wavelength spectrum. Monitor 247 of computer2 43 serves as the display for the spectral composition. Selection of the wavelength spectrum together with its spectral composition is accomplished on the basis of a graph G within a coordinate system having two coordinate axes X, Y. The wavelength of the light is plotted on coordinate axis X, and its power level on coordinate axis Y. Computer 243 controls high-frequency source 239 in accordance with the user's stipulation. The user makes adjustments using computer mouse 257. Depicted on monitor 247 is a slider 259 that serves for adjustment of the overall light power level of illuminating light beam 11 or detected light beam 229.

Although embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

The invention claimed is:

1. A spectral engine light source for supplying light to an apparatus, comprising:
    a microstructured delivery fiber assembly configured for delivering broad band light and comprising a microstructured delivery fiber and a connector member, said delivery fiber having a longitudinal axis, an input end for launching light and a delivery end for delivering light, said delivery fiber comprises a core region and a cladding region surrounding the core region, wherein the cladding region comprises a cladding background material having a refractive index Nbg and a plurality of inclusions of solid material having a refractive index up to Ninc and extending in the direction of longitudinal axis of the delivery fiber, wherein Ninc<Nbg and the plurality of inclusions in the cladding region is arranged in a cross-sectional pattern comprising at least two rings of inclusions surrounding the core region, said core region having a diameter up to about 15 µm, said connector member being mounted to said delivery fiber at a delivery end section of the delivery fiber, said delivery fiber defining a bandwidth of about 200 nm or more in which a transmission loss is less than 0.5 dB/m at all wavelengths within the bandwidth,
    said spectral engine light source further comprising a spectral engine, said spectral engine comprising
        two or more lasers emitting respective laser beams, said with wavelength(s) that differ with at least one wavelength; and
        a multiplexer, wherein the multiplexer is configured for receiving at least a portion of the laser beams of each of the lasers and for collimating the received light to a multiplexed beam, and wherein said microstructured delivery fiber is arranged to receive said multiplexed beam and to deliver at least a part of said received multiplexed beam to the apparatus.

2. The spectral engine light source of claim 1, wherein an inclusion of said plurality of inclusions has a higher refractive index than another inclusion of said plurality of inclusions.

3. The spectral engine light source of claim 1, wherein one of said laser beams of said spectral engine emitted from said two or more lasers comprises at least one wavelength below 500 nm and one of said laser beams emitted from said two or more lasers comprises at least one wavelength above 800 nm.

4. The spectral engine light source of claim 1, wherein at least one of said laser beams of said spectral engine emitted from said two or more lasers has a bandwidth of about 50 nm or less.

5. The spectral engine light source of claim 1, wherein the apparatus comprises an illumination apparatus configured for illuminating a target.

6. The spectral engine light source of claim 1 wherein said two or more lasers comprise at least three lasers, wherein a first laser of the lasers is adapted for emitting a laser beam comprising at least one wavelength below 450 nm, a second laser of the lasers is adapted for emitting a laser beam comprising at least one wavelength in the range from 500 nm to 700 nm, and a third of the lasers is adapted for emitting a laser beam comprising at least one wavelength above 800 nm.

* * * * *